United States Patent
Park et al.

(10) Patent No.: US 7,498,313 B2
(45) Date of Patent: Mar. 3, 2009

(54) LARGE CIRCULAR TARGET-SPECIFIC ANTISENSE NUCLEIC ACID COMPOUNDS

(75) Inventors: Jong-Gu Park, Daegu (KR); Ik-Jae Moon, Daegu (KR)

(73) Assignee: Welgene, Inc., Joongu, Daegu (KR)

( * ) Notice: Subject to any disclaimer, the term of this patent is extended or adjusted under 35 U.S.C. 154(b) by 0 days.

(21) Appl. No.: 10/066,498

(22) Filed: Jan. 30, 2002

(65) Prior Publication Data

US 2002/0182181 A1    Dec. 5, 2002

(51) Int. Cl.
*C07H 21/02* (2006.01)
*C07H 21/04* (2006.01)
*A61K 31/70* (2006.01)
*C12N 5/00* (2006.01)
*C12Q 1/68* (2006.01)

(52) U.S. Cl. .................. 514/44; 435/6; 435/320.1; 435/375; 435/377; 536/23.1; 536/24.5

(58) Field of Classification Search .............. 435/6, 435/325, 375; 536/23.1, 24.5; 514/44
See application file for complete search history.

(56) References Cited

U.S. PATENT DOCUMENTS 6,054,299 A * 4/2000 Conrad .................. 435/91.1
6,107,062 A * 8/2000 Hu et al. ................. 435/91.41

FOREIGN PATENT DOCUMENTS

WO    WO 98/38300    *    9/1998

OTHER PUBLICATIONS

Hellmann et al. Virology. 1985 143:23-34.*
Moon et al. J Biol. Chem. 2000. 275(18):4647-4653.*
Yamakawa, H et al. Nucleosides & Nucleotides, (1995) vol. 14, No. 3-5, pp. 1149-1152.*
LaPlante et al. Biochem J. 2000. 348:189-199.*
Flanagan, WM et al., Nucl. Acids Res. 1996, 24(15) 2936-2941.*
Gewirtz et al., 1996. Proc. Natl. Acad. Sci. v 93, pp. 3161-3163.*
Akhtar et al. *Life Sci.*, 49, 1793-1801 (1991).
Alberts et al. *Molecular Biology of the Cell*, Garland, New York, 1273-1290 (1994).
Anfossi et al. *Proc. Natl. Acad. Sci. USA*, 86, 3379-3383 (1989).
Baker et al. *Biochim. Biophys. Acta*, 1489, 3-18 (1999).
Bayever et al. *Antisense Res. Dev.* 3(4), 383-90 (1993).
Brand et al. *J. Clin. Invest.*, 97, 1715-1722 (1996).
Camenisch et al. *J. Immunol.*, 162(6), 3498-503 (1999).
Collins et al. *FASEB J.*, 9, 899-909 (1995).
Collins *Lab Invest.*, 68, 499-508 (1993).
De Backer et al. *Nat. Biotechnol.*, 19, 235-241 (2001).
Defillipi et al. *Curr Top Microbiol. Immunol.*, 184, 87-98 (1993).
Dolnick *Cancer Invest.*, 9, 185-194 (1991).
Eilers et al. *Nature*, 340, 66-68 (1989).
Ferrari et al. *Cell Growth Differ.*, 1, 543-548 (1990).
Flanagan et al. *Mol. Cell Biochem.*, 172, 213-225 (1997).
Gryaznov et al. *Nucleic Acids Res.*, 24, 1508-1514 (1996).
Heikkila et al. *Nature*, 328, 445-448 (1987).
Helene *Eur. J. Cancer*, 27(11), 1466-71 (1991).
Henriksson et al. *Adv. Cancer Res.*, 68, 109-182 (1996).
Hill et al. *J. Immunol.*, 164(2), 656-63 (2000).
Ji et al. *Science*, 293, 2266-2269 (2001).
Jupin et al. *Nucleic Acid Res.*, 23, 535-536 (1995).
Kamano et al. *Leuk. Res.*, 14, 831-839 (1990).
Kastan et al. *Blood*, 74, 1517-1524 (1989).
Matsuda et al. *Mol. Biol. Cell*, 7, 1095-1106 (1996).
Melani et al. *Cancer Res.*, 51, 2897-2901 (1991).
Melotti et al. *Blood*, 87, 2221-2234 (1996).
Moon et al. *Biochem. J.*, 346, 295-303 (2000).
Moon et al. *J. Biol. Chem*, 275(7), 4647-53 (2000).
Morgan *Nature* (Lond.), 374, 131-134 (1995).
Nesterova et al. *Nat. Med.*, 1, 528-533 (1995).
Ohtsubo et al. *Mol. Cell. Biol.*, 15, 2612-2624 (1994).
Offensperger et al. *EMBO J.*, 12, 1257-1262 (1993).
Packham et al. *Biochim. Biophys., Acta*, 1242, 11-28 (1995).
Perkins et al. *Arthritis Rheum.*, 41(12), 2205-10 (1998).
Ratajczak et al. *Blood*, 79, 1956-1961 (1992).
Roush *Science*, 276, 1192-1193 (1997).
Sawyers et al. *Cell*, 70, 901-910 (1992).
Sherr *Cell*, 73, 1059-1065 (1993).
Thaler et al. *Proc. Natl. Acad. Sci. USA*, 93, 1352-1356 (1996).
Thanos et al. *Cell*, 80, 529-532 (1995).
Thompson et al. *Nature*, 314, 363-366 (1985).
Tomita et al. *Hypertension*, 26, 131-136 (1995).
Wagner *Nature*, 372, 333-335 (1994).
Wagner et al. *Science*, 260, 1510-1513 (1993).
Young et al. *Proc. Natl. Acad. Sci. USA*, 88, 10023-10026 (1991).

* cited by examiner

*Primary Examiner*—Sean R McGarry
(74) *Attorney, Agent, or Firm*—Joseph Hyosuk Kim; JHK Law

(57) ABSTRACT

The present application describes a large circular target-specific antisense molecule that is effective in ablating RNA and protein expression. The large circular antisense molecule is used to treat any human disease in which modulation of gene expression can be beneficial to intervene in the disease initiation and progression.

29 Claims, 11 Drawing Sheets

Single strand rescue by helper bacteriophages (SEQ ID NO: 29)

A

B

A

B

C

D

LARGE CIRCULAR TARGET-SPECIFIC ANTISENSE NUCLEIC ACID COMPOUNDS

CONTINUING DATA

The present application claims the benefit of priority to PCT/KR01/01730, filed Oct. 13, 2001, the contents of which are incorporated herein in its entirety.

BACKGROUND OF THE INVENTION

1. Field of the Invention

The present invention relates to the field of antisense technology. The present invention also relates to using the antisense technology in therapeutics and in gene function identification systems.

2. Description of the Background

Antisense molecules bind to complementary sequences of mRNA through Watson-Crick base pairing. Antisense oligonucleotides (AS-oligos) have been valuable in the functional study of a gene by reducing gene expression in sequence specific manner (Thompson et al. *Nature*, 314, 363-366 (1985); Melani et al. *Cancer Res.*, 51, 2897-2901 (1991); Anfossi et al. *Proc. Natl. Acad. Sci. USA*, 86, 3379-3383 (1989)). Intense effort has also been made to develop antisense anticancer agents that eliminate aberrant expression of genes involved in tumor initiation and progression (Kamano et al. *Leuk. Res.*, 14, 831-839 (1990); Melotti et al. *Blood*, 87, 2221-2234 (1996); Ferrari et al. *Cell growth Differ.*, 1, 543-548 (1990); Ratajczak et al. *Blood*, 79, 1956-1961 (1992); Kastan et al. *Blood*, 74, 1517-1524 (1989); Thaler et al. *Proc. Natl. Acad. Sci. USA*, 93, 1352-1356 (1996); Wagner *Nature*, 372, 333-335 (1994)). Synthetic AS-oligos have been widely utilized for their ease of design and synthesis as well as potential specificity to a target gene. Antisense inhibition of gene expression is believed to be achieved either through RNaseH activity following the formation of antisense DNA-mRNA duplex or through steric hindrance of the mRNA movement to bind a ribosomal complex (Dolnick *Cancer Invest.*, 9, 185-194 (1991)). There has also been an effort to inhibit gene expression by employing oligonucleotides that form triple helix aimed at the promoter region of the genomic DNA. Moreover, duplexed oligonucleotide decoys that compete with the promoter region of genomic DNA has also been formed (Young et al. *Proc. Natl. Acad. Sci. USA*, 88, 10023-10026 (1991)). Efficacy of AS-oligos has been validated in animal models as well as several recent clinical studies (Offensperger et al. *EMBO J.*, 12, 1257-1262 (1993); Tomita et al. *Hypertension*, 26, 131-136 (1995); Nesterova et al. *Nat. Med.*, 1, 528-533 (1995); Roush *Science*, 276, 1192-1193 (1997)). In addition, the first antisense drug was approved for CMV retinitis in US and Europe.

Expectations for AS-oligos have, however, frequently met with disappointment, as results have not always been unambiguous. Some of the problems of using AS-oligos have been inaccessibility to a target site (Flanagan et al. *Mol. Cell Biochem.*, 172, 213-225 (1997); Matsuda et al. *Mol. Biol. Cell*, 7, 1095-1106 (1996)), instability to nucleases (Akhtar et al. *Life Sci.*, 49, 1793-1801 (1991); Wagner et al. *Science*, 260, 1510-1513 (1993); Gryaznov et al. *Nucleic Acids Res.*, 24, 1508-1514 (1996)), lack of sequence specificity and various side effects in vivo. The stability of AS-oligos has improved to a certain extent by using chemically modified oligos, which are the so-called second generation AS-oligos (Helene *Eur J Cancer*, 27(11),1466-71 (1991); Bayever et al. *Antisense Res. Dev.* 3(4), 383-90 (1993); Baker et al. *Biochim. Biophys. Acta.*, 1489, 3-18 (1999)). Phosphorothioate (PS)- and methylphosphonate (MP)-oligos, have been exhaustively studied and are utilized mainly to augment stability to nucleases. However, each of the modified AS-oligos exhibit both lack of sequence specificity and insensitivity to RNaseH. Further, there has been concern over inadvertent introduction of mutations during DNA replication or repair caused by recycling of hydrolyzed modified nucleotides.

A series of distinct antisense molecules with enhanced stability, the so-called 'third generation AS-oligos', having 1) a stem-loop structure, 2) the CMAS (Covalently-closed Multiple Antisense) structure and 3) the RIAS (Ribbon Antisense) structure (Moon et al. *Biochem J.*, 346, 295-303 (2000); Matsuda et al. *Mol. Biol. Cell*, 7, 1095-1106 (1996); Moon et al. *J. Biol Chem.*, 275(7), 4647-53 (2000)) have been described. Both CMAS and RiAS-oligonucleotides exhibit enhanced stability to exonucleases and nucleases in biologic fluids. These antisense molecules are also efficacious in the specific reduction of target mRNA. However, there is a need in the art to develop an antisense molecule with greater facility and enhanced binding efficiency.

Certain bacteriophages, such as M13 bacteriophage, have a single stranded circular genome, which has been employed for DNA sequencing analyses as well as mutagenesis studies. M13 phagemid, which is a plasmid used in the construction of a recombinant bacteriophage, can be engineered to produce a large quantity of circular single stranded genomic DNA that contains an antisense sequence to a specific gene. This approach for producing antisense DNA takes advantage of the stability to exonucleases associated with the covalently closed structure, high sequence fidelity, elimination of laborious target site search and easy construction of an antisense library.

Tumor Necrosis Factor alpha (TNF-α) is a cytokine required for normal immune response (Perkins et al. *Arthritis Rheum.*, 41(12), 2205-10 (1998)), septic shock (Camenisch et al. *J. Immunol.*, 162(6), 3498-503 (1999)), and graft versus host response when produced in excess (Hill et al. *J. Immunol.*, 164(2), 656-63 (2000)). TNF-α is also a typical proinflammatory cytokine and is closely linked with rheumatoid arthritis, allergy and other immunological disorders including sepsis and inflammatory conditions (Perkins et al. *Arthritis Rheum.*, 41(12), 2205-10 (1998)). TNF-α expression can be induced in rat monocytic cell line WRT7/P2 by lipopolysaccharide (LPS) treatment.

Nuclear factor-κB (NF-κB) regulates a variety of genes for cytokines (Collins *Lab Invest.*, 68, 499-508 (1993)); Collins et al. *FASEB J.*, 9, 899-909 (1995) and adhesion receptors (Thanos et al. *Cell*, 80, 529-532 (1995)). Activated NF-κB was identified in macrophages, smooth muscle cells and endothelial cells of human artherosclerotic tissue (Defillipi et al. *Curr Top Microbiol Immunol.*, 184, 87-98 (1993)) suggesting an important role of NF-κB in inflammatory and proliferative processes (Brand et al. *J Clin Invest.*, 97, 1715-1722 (1996)).

The ras oncogene is frequently activated in human neoplasms. RAS p21 proteins are a part of the large family of GTP/GDP-binding proteins, located on the inner side of the plasma membrane. A point mutation in the ras gene can create a RAS p21 protein that fails to hydrolyze its bound GTP and thus transmits an intracellular signal resulting in unregulated cell proliferation (Alberts et al. *Molecular biology of the cell. Garland, New York,* 1273-1290 (1994)).

The protooncogene c-myb plays an important role in the proliferation and differentiation of hematopoietic cells. Hematopoietic cells show differential expression of c-myb and exhibit little expression of the gene upon terminal differentiation (Melotti et al. *Blood*, 87, 2221-2234 (1996); Ferrari et al. *Cell growth Differ.*, 1, 543-548 (1990)). The c-myb gene product has been frequently found to be overexpressed in leukemic cells (Melani et al. *Cancer Res.*, 51, 2897-2901 (1991); Anfossi et al. *Proc. Natl. Acad. Sci. USA*, 86, 3379-3383 (1989); Kamano et al. *Leuk. Res.*, 14, 831-839 (1990)).

The MYC oncoproteins play a central role in tumor cell growth (Packham et al. *Biochim. Biophys. Acta.*, 1242, 11-28 (1995); Henriksson et al. *Adv. Cancer Res.*, 68, 109-182 (1996)). MYC is sufficient to induce quiescent cells to enter the cell cycle (Eilers et al. *Nature*, 340, 66-68 (1989)), suggesting that it is required for continuous cell growth, while its inhibition can intervene in mitogenic signaling and induce cells to differentiate terminally (Heikkila et al. *Nature*, 328, 445-448 (1987); Sawyers et al. *Cell*, 70, 901-910 (1992)).

The principal components of the cell cycle regulatory genes are represented by a family of protein kinases termed cyclin-dependent kinases (CDKs). A greater understanding of molecular events controlling the transition from one phase of cell cycle to the next has engendered the discovery of CDKs (Morgan *Nature (Lond.)*, 374, 131-134 (1995)). CDKs are inactive until they bind to their coactivators, which are individual cyclin proteins. As cells enter $G_1$, kinase activities of CDK4 and CDK6 appear necessary for transition through early $G_1$ checkpoints (Sherr *Cell*, 73, 1059-1065 (1993)), and the activity of the CDK2-cyclin E complex is necessary for transition from $G_1$ into S phase (Ohtsubo et al. *Mol. Cell. Biol.*, 15, 2612-2624 (1994)). The development of potent antisense oligonucleotides for CDK activity would represent an attractive approach for the inhibition of tumor cell growth.

There is a need in the art for more specific, stable and potent antisense molecules to be used against various human diseases.

SUMMARY OF THE INVENTION

The claimed invention overcomes the above-mentioned problems, and provides antisense molecules, compositions of antisense molecules, a method of making the antisense molecules, and a method of using the claimed molecules and compositions which provide the advantage of inhibiting or significantly modifying the expression of certain targeted genes. In the case that expression of these targeted gene(s) is responsible for causing cancer, then administering the inventive antisense molecules to the cells will result in the ablation of the target RNA, which will inhibit proliferation of the cells, which in turn will result in curing or at least improving the survival associated with the cancer.

It is to be understood that the invention is not limited to treating cancer. The principles of the antisense compound of the invention may be applied to efficiently ablate any target RNA. Any phenotypic manifestation of this chemical activity in the form of cancer treatment, eliminating adverse effects of viral infection, treating metabolic diseases, immunologic disorders, and so on are a result of the antisense therapy.

The invention further includes compositions of the claimed antisense molecules together with a pharmaceutically acceptable carrier.

The present invention is directed to a large circular nucleic acid molecule comprising a target-specific antisense region, which specifically binds to a portion of RNA expressed from a gene, wherein said antisense molecule is effective for reducing the expression of said gene. The large circular nucleic acid molecule may be at least about 3,000 nucleotides long, and the antisense region of the molecule may be at least about 50 nucleotides long, preferably at least about 100 nucleotides long. Further, the antisense region may be substantially complementary to an entire gene sequence.

In one embodiment of the invention, the large circular nucleic acid molecule may be a single stranded form of a recombinant bacteriophage or phagemid genome, such as a filamentous phage, and in particular, phage M13.

In another embodiment of the invention, a vector is disclosed that comprises the large circular nucleic acid molecule as described above. The vector may be derived from a filamentous phage. In still another embodiment of the invention, host cell comprising the vector is disclosed.

The present invention is also directed to a composition comprising a large circular nucleic acid molecule comprising a target-specific antisense region, which specifically binds to a portion of RNA expressed from a gene, wherein said antisense molecule is effective for reducing the expression of said gene, and a pharmaceutically acceptable carrier thereof.

In yet another embodiment of the invention, a method is disclosed for inhibiting expression of a selected protein by a large circular nucleic acid molecule targeted to an RNA encoding the selected protein, wherein the method includes targeting the nucleic acid molecule to the RNA such that the nucleic acid molecule hybridizes with the RNA to form a duplex with the RNA, wherein the duplex inhibits expression of the selected protein. The target protein may cause cell proliferation or cancer. And the cancer may be, but not limited to, leukemia, lung cancer, liver cancer, colon cancer, stomach cancer, pancreatic cancer, brain cancer or prostate malignancy. In particular, the cancer may be leukemia, cervical cancer, or breast cancer.

Alternatively, the target protein may be a tumor necrosis factor, nuclear factor, MYB, MYC, RAS, or cell division kinase. And if the target protein is a viral protein, the virus may be, but not limited to, herpes, human papilloma virus (HPV), HIV, small pox, mononucleosis (Epstein-Barr virus), hepatitis, or respiratory syncytial virus (RSV).

The target protein may cause a metabolic disease or an immunological disorder. If a metabolic disease, then it may be, but not limited to, phenylketonuria (PKU), primary hypothyroidism, galactosemia, abnormal hemoglobins, types I and II diabetes, or obesity. And if an immunological disorder, then it may be, but not limited to, Sjogren's Syndrome, antiphospholipid syndrome, immune complex diseases, Purpura, Schoenlein-Henoch, immunologic deficiency syndromes, systemic lupus erythematosus, immunodeficiency, rheumatism, kidney, or liver sclerosis.

The present invention is also directed to a chimeric large circular nucleic acid molecule comprising target-specific antisense regions, which specifically bind to a plurality of target RNA expressed from a plurality of target genes, wherein said nucleic acid molecule is effective for reducing the expression of said genes. In addition, a composition comprising the chimeric large circular nucleic acid molecule and a pharmaceutically acceptable carrier is also disclosed.

The invention is also directed to a method for inhibiting expression of a plurality of selected proteins by a large circular nucleic acid molecule targeted to a plurality of RNA molecules encoding a plurality of selected proteins comprising, (i) generating a chimeric large circular nucleic acid molecule comprising target-specific antisense regions targeted to said plurality of target RNA; and (ii) targeting the plurality of RNA such that the chimeric large circular nucleic acid molecule hybridizes with said RNA to form a duplex, wherein the duplex reduces expression of the plurality of selected proteins.

Still further, the invention is directed to a method for inhibiting cell proliferation, comprising, administering to said cell, a large circular nucleic acid molecule that comprises one or more antisense region substantially complementary to one or more target gene, in which inhibiting expression of said gene or genes inhibits cell proliferation.

In yet another embodiment, a method is disclosed for making a large circular nucleic acid molecule comprising target-specific antisense region which inhibits expression of a selected protein, comprising, (i) inserting a target-specific DNA of interest into a phage or phagemid genome;

(ii) allowing the phage to generate a single stranded form, which is the large circular nucleic acid molecule; and (iii) isolating said large circular nucleic acid molecule by gel filtration column.

The invention also provides a method of screening for a function of a gene comprising, (a) generating a large circular nucleic acid molecule comprising an antisense region that is substantially complementary to an RNA expressed from a cell;

(b) contacting a cell with the large circular nucleic acid molecule such that the antisense molecule enters the cell and hybridizes to an RNA expressed in the cell to inhibit expression of its gene product; and (c) assaying the cell for a variation of a phenotype.

In the above method, steps (a) to (c) may be applied to a library of said large circular nucleic acid molecules. Furthermore, in the method the nucleic acid molecule may be the single stranded form of a recombinant bacteriophage or phagemid genome.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

FIGS. 8A-8D show the effects of c-myc-M13AS, c-myb-M13AS, k-ras-M13AS and cdk2-M13AS on mRNA expression of their respective genes. K562 and HL-60 cells were transfected with c-myc-M13AS and c-myb-M13AS molecules, respectively. A. RT-PCR results on K562 cells. Lanes 1-2, c-myc-M13AS (0.56 nM and 1.12 nM, respectively); lanes 3-4, c-myc-M13SE (0.56 nM and 1.12 nM, respectively); and lane 5, M13SS (0.56 nM). B. RT-PCR results on HL-60 cells. Lanes 1-2, c-myb-M13AS (0.56 nM and 1.12 nM, respectively); and lanes 3-4, c-myb-M13SE (0.56 nM and 1.12 nM, respectively). C and D. HeLa cells were treated with different amounts of k-ras-M13AS and cdk2-M13AS molecules, respectively. C. Lanes 1-2, k-ras-M13AS (0.28 nM and 0.84 nM, respectively); lanes 3-4, k-ras-M13SE (0.28 nM and 0.56 nM, respectively); and lanes 5-6, M13-SS (0.28 nM and 0.56 nM, respectively). D. Lanes 1-3, cdk2-M13AS (0.28 nM, 0.56 nM and 0.84 nM, respectively); and lanes 4-6, cdk2-M13SE (0.28 nM, 0.56 nM and 0.84 nM, respectively). Amplified PCR fragments were electrophoresed on a 1% agarose gel and visualized with ethidium bromide staining.

Figure 9:
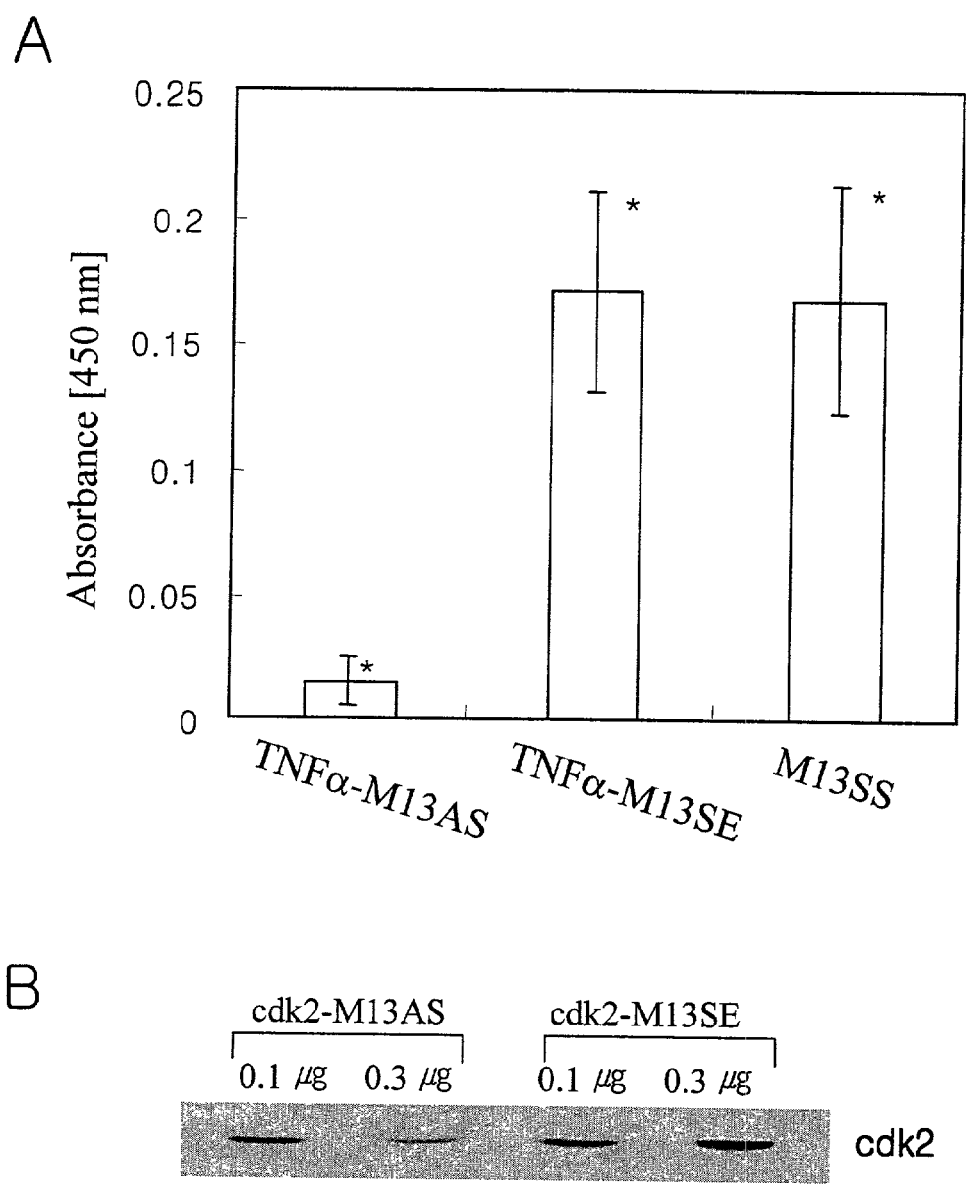

FIGS. 9A and 9B show reduced expression of TNFα and CDK2 by administering phage genomic antisense molecules. A. TNF-α released into media was measured using ELISA. WRT7/P2 cells were transfected with TNFα-M13AS, TNFα-M13SE or M13SS (lanes 1-3, respectively). TNF-α was induced with 30 μg/ml LPS for 6 hours. Supernatants from the cell cultures were diluted 50 fold immediately before the assay. Each bar value represents the mean ± S.D. of triplicate experiments. Statistical significance was calculated with student's t-test (analysis of variance, * $p<0.05$). B. Western blot analysis of CDK2 in HeLa cells alter the treatment of cdk2-M13AS molecules.

FIGS. 10A and 10B show the effects of phage genomic antisense molecules on proliferation of MCF-7 and HeLa cells. MTT assays were performed to determined growth inhibition of cells treated with k-ras-M13AS and cdk2-M13AS, respectively. A. MCF-7 cells were treated with 0.28 nM or 0.56 nM k-ras-M13AS complexed with Lipofectamine 2000 in a ratio of 1:3 (w/w): □ is k-ras-M13AS; ▒ is k-ras-M13SE; ▨ is naked k-ras-M13AS alone; and ■ is Lipofectamine 2000 reagent alone. B. HeLa cells were treated with cdk2-M13AS (0.84 nM) complexed with Lipofectamine 2000. Column 1, cdk2-M13AS (0.84 nM); column 2, cdk2-M13SE (0.84 nM); column 3, cdk2-M13AS without liposomes; and column 4, Lipofectamine 2000 alone. Each bar value represents the mean ± S.D. of triplicate experiments.

FIGS. 11A and 11B show the effects of c-myb-M13AS molecules on proliferation of K562 and HL-60 cells. MTT assay was performed to examine growth inhibition by c-myb-M13AS. Two kinds of c-myb-M13AS molecules were constructed, c-myb-M13AS1 and c-myb-M13AS2 containing either 0.5kb or 1.5kb of the c-myb sequence, respectively. K562 (A) and HL-60 (B) cells were treated with c-myb-M13AS (0.84 nM) complexed with Lipofectamine 2000. Column 1, c-myb-M13AS 0.5kb; column 2, c-myb-M13AS 1.5kb; column 3, c-myb-M13SE 1.5kb; and column 4, naked c-myb-M13AS 1.5kb alone. Each bar value represents the mean ± S.D. of triplicate experiments.

DETAILED DESCRIPTION OF THE INVENTION

The present invention is based on the discovery that a large circular nucleic acid molecule that includes a target-specific antisense region, especially those generated from a bacteriophage is useful as an effective ablator of gene expression.

In the present application, "a" and "an" are used to refer to both single and a plurality of objects.

As used herein, the term "antisense" means antisense nucleic acid (DNA or RNA) and analogs thereof and refers to a range of chemical species having a range of nucleotide base sequences that recognize polynucleotide target sequences or sequence portions through hydrogen bonding interactions with the nucleotide bases of the target sequences. The target sequences may be single- or double-stranded RNA, or single- or double-stranded DNA.

Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of molecules may be polymers in which the sugar moiety has been modified or replaced by another suitable moiety, resulting in polymers which include, but are not limited to, morpholino analogs and peptide nucleic acid (PNA) analogs. Such analogs include various combinations of the above-mentioned modifications involving linkage groups and/or structural modifications of the sugar or base for the purpose of improving RNaseH-mediated destruction of the targeted RNA, binding affinity, nuclease resistance, and or target specificity.

As used herein, "antisense therapy" is a generic term, which includes specific binding of large circular nucleic acid molecules that include an antisense segment for a target gene to inactivate undesirable target DNA or RNA sequences in vitro or in vivo.

As used herein, "cell proliferation" refers to cell division. The term "growth," as used herein, encompasses both increased cell numbers due to faster cell division and due to slower rates of apoptosis, i.e. cell death. Uncontrolled cell proliferation is a marker for a cancerous or abnormal cell type. Normal, non-cancerous cells divide regularly, at a frequency characteristic for the particular type of cell. When a cell has been transformed into a cancerous state, the cell divides and proliferates uncontrollably. Inhibition of proliferation or growth modulates the uncontrolled division of the cell.

As used herein, "chimeric large circular nucleic acid molecule" refers to a large circular nucleic acid molecule comprising a plurality of antisense nucleotide segments that are substantially complementary to a plurality of target genes. The segments of antisense nucleotides may be connected or linked to each other directly or indirectly by use of spacers between each segment.

As used herein, "filamentous phage" is a vehicle for producing the large circular nucleic acid molecule of the invention. Phages or phagemids may be used. In this instance, the desired sequence is inserted or cloned into the vehicle so that when a single strand is generated by the phage or phagemid, the large circular nucleic acid molecule is generated. DNA or RNA bacteriophage may be used for this purpose. In particular, filamentous bacteriophage may be used. Filamentous phages such as M13, fd, and fl have a filamentous capsid with a circular ssDNA molecule. Their life-cycle involves a dsDNA intermediate replicative form within the cell which is converted to a ssDNA molecule prior to encapsidation. This conversion provides a means to prepare ssDNA. The bacteriophage M13 has been adapted for use as a cloning vector.

As used herein, a "gene" refers either to the complete nucleotide sequence of the gene, or to a sequence portion of the gene.

As used herein, the terms "inhibiting" and "reducing" are used interchangeably to indicate lowering of gene expression or cell proliferation or any other phenotypic characteristic.

As used herein, "large circular nucleic acid molecule" also referred to as "large circular antisense molecule" is a single stranded molecule, which includes at least one antisense region that is substantially complementary to and binds a target gene or RNA sequence, which inhibits or reduces expression of the gene as well as, in some instances, its isoforms. The circular single stranded nucleic acid molecule may contain either sense or antisense sequence for one or several genes, so long as the sequence for the target gene is in the antisense form.

Large circular nucleic acid molecule may be synthesized by chemical methods. But typically, it is produced from a filamentous phage system, which includes M13 and phagemids that are derived from it. When the large circular nucleic acid molecule is generated from a phage, it may also be referred to as a "phage genomic antisense compound".

In one sense, the large circular nucleic acid molecule is longer than a typical oligonucleotide sequence that may be about 20 to 30 nucleoltides long. In contrast, the large circular nucleic acid molecule may be at least 3,000 nucleotides long. Typically, the range may be from about 3,000 to about 8,000 nucleotides long. Although a length of about 3,100 to about 7,000 nucleotides may be useful in the invention, preferred length range may be from about 3,300 to about 6,000 bases.

Alternatively, it is understood that there does not have to be an absolute upper or lower limit to the length of the large circular nucleic acid molecule. This is especially so when a phage is used to generate the large circular nucleic acid molecule, in which case the size of the phage and the size of the insert that encodes at least a portion of the target gene may control the length of the single stranded nucleic acid generated. Thus, in one embodiment, the nucleic acid molecule may be as long as a phage such as a filamentous phage may accommodate.

The large circular nucleic acid molecule may contain both the specific antisense sequence as well as extraneous sequence. Extraneous sequence may include sense or antisense forms of various other genes. Or, if a phage is used to generate the nucleic acid molecule, the extraneous sequence may be the vector sequence. The length of the target-specific antisense region of the large circular nucleic acid molecule may be without limitation from a bit lower than about 100 nucleotides to over about 5,000 bases. Typically, the range may be from about 200 to about 3,000. In particular, the range may be about 400 to about 2,000. The target-specific antisense region may be also complementary to an entire gene.

In another embodiment, the antisense molecule may be generated from the genome of a bacteriophage as part of the natural life cycle of the phage.

As used herein, "substantially complementary" means an antisense sequence having about 80% homology with an antisense compound which itself is complementary to and specifically binds to the target RNA. As a general matter, absolute complementarity may not be required. Any antisense molecule having sufficient complementarity to form a stable duplex or triplex with the target nucleic acid is considered to be suitable. Since stable duplex formation depends on the sequence and length of the hybridizing antisense molecule and the degree of complementarity between the antisense molecule and the target sequence, the system can tolerate less fidelity in complementarity with large circular molecule.

As used herein, "target" or "targeting" refers to a particular individual gene for which an antisense molecule is made. In an embodiment of the invention, the antisense molecule is made from an insert in a LC-antisense compound. In certain contexts, "targeting" means binding or causing to be bound the antisense molecule to the endogenously expressed transcript so that target gene expression is eliminated. The target nucleotide sequence may be selected from genes involved in various malignancies, including genes involved in the initiation and progression of various diseases such as immune diseases, infectious diseases, metabolic diseases and hereditary diseases or any other disease caused by abnormal expression of genes.

The antisense molecule of the invention was found to be superior to conventional synthetic AS-oligos in biochemical and biologic activities. While conventional AS-oligos can be easily synthesized by a DNA synthesizer, they require the selection of a target site. The process of selecting for the target site is sometimes termed 'AS-oligo design'. This process is time consuming and often inconclusive. In addition, synthesized AS-oligos are unstable to nucleases, have frequent sequence errors, entail high production cost, and exhibit poor cellular uptake even after complexation with liposomes.

In an embodiment of the invention, a single stranded circular genomic DNA generated from a bacteriophage, which is used as an antisense vector is disclosed. In particular, the bacteriophage that is used may be M13 phage or any modified form thereof. But it is understood that any bacteriophage or plasmid, virus or any cloning vehicle that generates single stranded nucleic acid may be used. Preferably, the generated single stranded nucleic acid is circular. The DNA molecule from which the antisense molecule is generated may be cloned into the genome of the vehicle, such as a bacteriophage.

Conventional wisdom in the field of antisense research has discouraged using long antisense molecules because it was thought that longer AS-oligos tend to be less specific, harder to synthesize and inefficient in cellular uptake. Indeed, chemically modified second generation AS-oligos such as phosphorothioate modified oligos, have reduced sequence specificity as the length of the AS-oligos is extended. Furthermore, synthesis of linear AS-oligos becomes increasingly difficult, and sequence fidelity declines markedly as the length of AS-oligo s increases.

The phage vector allows easy production of the long single stranded sequence that encompasses the antisense sequence with high sequence fidelity. The inventive antisense molecules, even with their unconventionally long length, exhibited good sequence specificity in eliminating expression of target mRNA. Without being bound by any particular theory or mechanism of action of the antisense nucleic acid, it is thought that once a small portion of the antisense sequence binds to its complementary sequence, the antisense sequence zips through the entire length of the complementary target sequence. The lengthy duplex formed between the antisense DNA and sense RNA is then much more stably maintained as a substrate for RNaseH activity.

Another reason for the advantageous binding of the inventive antisense molecule may be that there may exist a higher chance for the long antisense molecule to bind to a target site that is structurally exposed. Messenger RNA tends to form extensive secondary and tertiary structures within its own sequence and by interaction with RNA binding proteins in the cell cytoplasm. Finding an open target site for an antisense molecule is critical for successful antisense activity. With its long length, the phage genomic antisense molecule has to have some sequence that can access exposed complementary sequences of target mRNA, thus improving the chances for target mRNA ablation.

The principles of the antisense molecules of the invention may be applied to any target gene of interest. While TNF-α, NFκB, c-myb, c-myc, cdk2, k-ras are disclosed as examples of using the antisense molecule of the invention, the antisense molecule of the invention may be made against any gene of interest. In fact, the antisense molecules of the invention were significantly more stable to nucleases and were effective in target ablation. Exemplified sequence specific reduction of TNF-α NFκB, c-myb, c-myc, cdk2, k-ras target genes supports the broad utility of the present antisense method. Thus, the antisense molecule of the invention may be used to bind to any target mRNA sequence from any source.

Antisense activity was also examined at the protein level to ensure correlation of both target mRNA and protein elimination. Administration of TNFα-M13AS was found to significantly reduce rat TNF-α secretion in cell culture media, confirming effective antisense activity. In contrast, control phage genomic compounds (single stranded circular molecules without an antisense insert) DNA exhibited only a mild reduction in TNF-α secretion. The slight decrease of TNF-α secretion by the addition of control antisense molecule can be explained, in part, by the cytotoxicity of free cationic liposomes deposited inside endosomes. Cells treated with cationic liposomes alone exhibited lower viability than cells with liposome-antisense molecule complex. Treatment with cdk2-M13AS resulted in similar ablation of CDK2 expression. Moreover, when gene specific antisense compounds of the invention were administered to c-myb and cdk2 bearing tumor cell lines, growth inhibition was observed.

Cellular uptake of conventional AS-oligos can be greatly enhanced when complexed with cationic liposomes. However, AS-oligos exhibit inconsistent and often inefficient cellular uptake upon forming complexes with different types of liposomes. In contrast, phage genomic antisense molecules form many short stem-loop structures due to its long length, behaving much like plasmid DNA. In fact, when complexed with several different types of liposomes, the antisense DNA showed consistent and enhanced cellular uptake (data not shown).

Synthetic AS-oligos usually have 15 to 25 nucleotide residues, and bind only to a single target site and eliminate substrate mRNA. However, most chronic human diseases show multiple genetic disorders that are in need of antisense molecules that can target multiple genes involved in the disease. In order to satisfy such a need, it is desired to devise an antisense molecule with multiple targeting ability. However, chemically synthesizing such a molecule would not be practical because of various obstacles in chemical synthesis. By using phage genomic DNA, multiple antisense sequences can be easily constructed by gene cloning. Further, the sequence integrity of the phage genomic DNA with multiple antisense sequences equals that of plasmid DNA amplified in bacterial cells.

Additional advantages with the phage genomic antisense molecule is the broad tolerance in sequence variation. The genomic antisense molecule of the invention may be effective as long as patches of identical sequences with more than about 15 consecutive nucleotides are conserved between different gene variants. This property is particularly useful in targeting polymorphic strains of pathogenic viruses such as HIV and HBV in which the same antisense molecule may be used against the variant forms. In addition, this type of phage genomic antisense molecule generated from one species such as humans may be used to study gene function in other species such as rodents, as long as the sequence divergene between the source and target organism is not spread evenly along the coding sequence.

Antisense molecules are also effective means to study the functions of genes by the so called "knockdown" approach (De Backer et al. *Nat. Biotechnol*, 19, 235-241 (2001); Ji et al. *Science,* 293, 2266-2269 (2001)). In the "knockdown" approach, gene function may be elucidated without destroying the gene. This strategy is faster than conventional "knockout" method used to identify gene function. The genomic antisense molecule in one embodiment of the invention, is uniquely suited for 'massive' functional genomics. Some of the salient features of using phage genomic antisense compounds for massive functional genomics are: 1) construction of antisense molecules which do not require elaborate antisense design, 2) construction of an antisense library with large individual member clones, and 3) superior antisense activity, thus avoiding data misinterpretation due to partial antisense activity.

By employing the phage genomic antisense method in one embodiment of the invention, the efficiency of the system as used in massive functional genomics is superior by several hundred fold to that of conventional AS-oligos method. Moreover, contrary to using other indirect systems, such as DNA chip, Serial Analysis of Gene Expression (SAGE), TIGR Orthologous Gene Alignment (TOGA) database, and proteomics, massive functional genomics employing the inventive phage genomic antisense system employs a direct gene functionalization system.

Circular antisense molecules made from a bacteriophage system and in particular, the M13 bacteriophage system or from an appropriate phagemid system is stable and efficient in blocking target gene expression. The phage genomic antisense molecule is effective in small amounts, but can also be prepared in large numbers. The inventive antisense molecules are effective therapeutic agents against various types of cancer, viral infection, immunologic disorders, metabolic disorders and other human diseases in which modulation of gene expression can be beneficial to intervene in disease initiation and progression.

In therapeutic applications, the large circular nucleic acid molecules can be formulated for a variety of modes of administration, including oral, topical or localized administration. Techniques and formulations generally may be found in Remington's Pharmaceutical Sciences, Mack Publishing Co., Easton, Pa., latest edition. The active ingredient that is the antisense molecule is generally combined with a carrier such as a diluent of excipient which may include fillers, extenders, binding, wetting agents, disintegrants, surface-active agents, erodable polymers or lubricants, depending on the nature of the mode of administration and dosage forms. Typical dosage forms include tablets, powders, liquid preparations including suspensions, emulsions and solutions, granules, and capsules.

Certain of the large circular nucleic acid compounds of the present invention may be particularly suited for oral administration which may require exposure of the drug to acidic conditions in the stomach for up to about 4 hours under conventional drug delivery conditions and for up to about 12 hours when delivered in a sustained release form. For treatment of certain conditions it may be advantageous to formulate these antisense compounds in a sustained release form.

Systemic administration of the large circular nucleic acid molecules may be achieved by transmucosal or transdermal means, or the compounds can be administered orally. For transmucosal or transdermnal administration, penetrants appropriate to the barrier to be permeated are used in the formulation. Such penetrants are generally known in the art, and include, for example, bile salts and fasidic acid derivatives for transmucosal administration. In addition, detergents may be used to facilitate permeation. Transmucosal administration may be through use of nasal sprays, for example, as well as formulations suitable for administration by inhalation, or suppositories.

The large circular nucleic acid molecule of the present invention can also be combined with a pharmaceutically acceptable carrier for administration to a subject. Examples of suitable pharmaceutical carriers are a variety of cationic lipids, including, but not limited to N-(1-2,3-dioleyloxy)propyl)-n,n,n-trimethylammonium chloride (DOTMA) and dioleoylphophotidyl ethanolamine (DOPE). Liposomes are also suitable carriers for the antisense molecules of the invention. Another suitable carrier is a slow-release gel or polymer comprising the claimed antisense molecules.

The large circular nucleic acid molecules may be administered to patients by any effective route, including intravenous, intramuscular, intrathecal, intranasal, intraperitoneal, intratumoral, subcutaneous injection, in situ injection and oral administration. Oral administration may require enteric coatings to protect the claimed antisense molecules and analogs thereof from degradation along the gastrointestinal tract. The large circular nucleic acid molecules may be mixed with an amount of a physiologically acceptable carrier or diluent, such as a saline solution or other suitable liquid. The antisense molecules may also be combined with other carrier means to protect the nucleic acid molecules or analogs thereof from degradation until they reach their targets and/or facilitate movement of the antisense molecules or analogs thereof across tissue barriers.

In one embodiment, the large circular nucleic acid molecules are administered in amounts effective to inhibit cancer or neoplastic cell growth. In other embodiments, the antisense molecule may be used to treat viral infections, such as, but not limited to herpes, human papilloma virus (HPV), HIV, small pox, mononucleosis (Epstein-Barr virus), hepatitis, respiratory syncytial virus (RSV) and so on. In addition, metabolic diseases, such as, but not limited to, phenylketonuria (PKU), primary hypothyroidism, galactosemia, abnormal hemoglobins, types I and II diabetes, obesity an so on are also targets. The inventive antisense molecule may be used to treat other diseases such as immunologic diseases including such diseases as, but not limited to, Sjogren's Syndrome, antiphospholipid syndrome, immune complex diseases, Purpura, Schoenlein-Henoch, immunologic deficiency syndromes, systemic lupus erythematosus, immunodeficiency, rheumatism, and so on.

The actual amount of any particular large circular nucleic acid molecule administered will depend on factors such as the type and stage of the disease or infection, the toxicity of the antisense molecule to other cells of the body, its rate of uptake by the cells, and the weight and age of the individual to whom the nucleic acid molecule is administered. An effective dosage for the patient can be ascertained by conventional methods such as incrementally increasing the dosage of the antisense molecule from an amount ineffective to inhibit cell proliferation to an effective amount. It is expected that concentrations presented to the diseased cells may range from about 0.1 nM to about 30 µM will be effective to inhibit gene expression and show an assayable phenotype. Methods for determining pharmaceutical/pharmacokinetic parameters in chemotherapeutic applications of antisense molecules for treatment of cancer or other indications are known in the art.

The large circular nucleic acid molecules are administered to the patient for at least a time sufficient to have a desired effect. To maintain an effective level, it may be necessary to administer the antisense nucleic acid molecules several times a day, daily or at less frequent intervals. For cancer cells, antisense molecules are administered until cancer cells can no longer be detected, or have been reduced in number such that further treatment provides no significant reduction in number, or the cells have been reduced to a number manageable by surgery or other treatments. The length of time that the antisense molecules are administered will depend on factors such as the rate of uptake of the particular molecule by cancer cells and time needed for the cells to respond to the molecule.

The following examples are offered by way of illustration of the present invention, and not by way of limitation.

EXAMPLES

Example 1

Materials and Methods

1. Cell Culture

Monocytic mouse cell line WRT7/P2 was used. Human cell lines, THP-1, HL-60 (acute promyelocytic leukemia), K562 (chronic myelogenous leukemia), HeLa (cervix cancer) and MCF-7 (breast cancer) were obtained from Korean Cell Line Bank (KCLB, Korea). These cell lines were maintained in either RPMI 1640 or EMEM (JBI, Korea) supplemented with 10% heat-inactivated FBS (JBI, Korea), 100 units/ml penicillin and 100 µg /ml streptomycin. Cells were cultured in a $CO_2$ (5%) incubator at 37° C. and carefully maintained to avoid over growth. Cells were exchanged with fresh culture media the day before lipofection and tested for cell viability with 0.4% trypan blue staining on the day of experiments.

2. Induced Expression of TNF-α mRNA and Cloning of Genes Encoding Rat TNF-α and Human NF-κB Rat TNF-α expression was induced with lipopolysaccharide (LPS, 30 µg/ml) in WRT7/P2 cells. Cells at $1\times10^5$ cells/well were seeded in each well of a 48-well plate and were treated with LPS. Cells were harvested at desired time points to examine the amounts of mRNA. The LPS incubation time by which TNF-α expression was induced at the highest level was chosen for further experiments.

Figure 1:
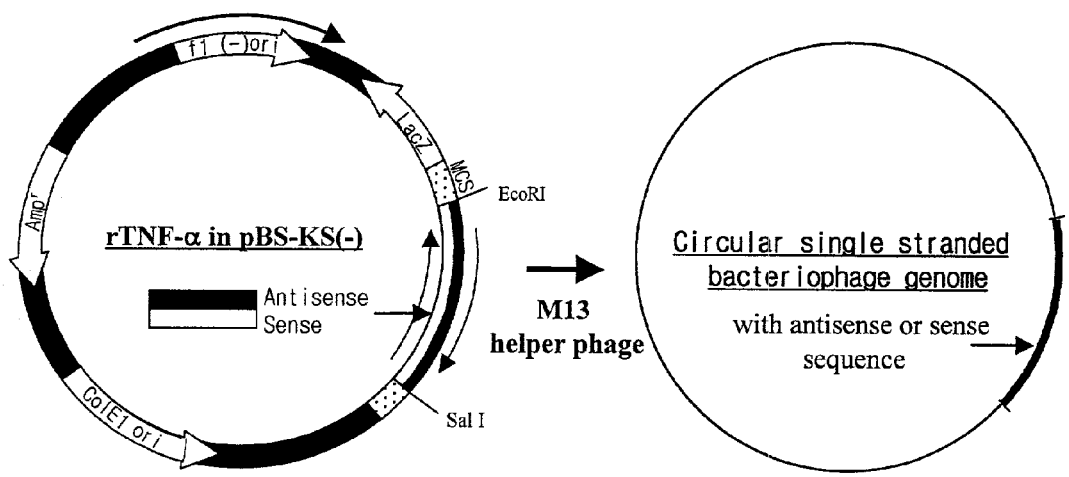
FIG. 1 shows a schematic diagram of the phage genomic circular antisense molecule of rat TNF-α (rTNFα-M13AS). Rat TNF-α was cloned into the multiple cloning site of the phagemid vector, pBS-KS(−). Whereas single stranded sense molecules were obtained by placing the TNF-α insert in the same orientation as that of the lacZ gene, antisense molecules were obtained by placing the TNF-α gene in reverse orientation to the lacZ gene. These constructs allow the rescue of either single stranded antisense or sense molecules of TNF-α when coinfected with a helper phage, M13KO7.

Rat TNF-α cDNA was obtained from the amplified cDNA fragments as described above. The RT-PCR fragment (708 bp) of TNF-α that comprises the entire coding sequence was amplified with a pair of PCR primers: 5'-GATCGTCGAC-GATGAGCACAGAAAGCATGATCC-3' (SEQ ID NO:1), and 5-GATCGAATTCGTCACAGAGCAATGACTC-CAAAG-3' (SEQ ID NO:2). The rat TNF-α cDNA fragment was cloned into the multiple cloning site of pBluescript (pBS) KS (–) vector using SalI and EcoRI restriction sites in the same direction as the lacZ gene (FIG. 1).

Similarly, cDNA fragments of the NF-κB, c-myb, c-myc, k-ras and cdk2 genes were amplified with a pair of PCR primers (Table 1) and cloned into the EcoRV site of pBS-KS (+) vector after blunting the ends. Amplified cDNA fragments were always confirmed with both restriction digestion and DNA sequencing.

3. Construction of Large Circular Nucleic Acid Molecules Employing a Phagemid Vector and the M13KO7 Helper Bacteriophages (1) Construction of single stranded bacteriophage genome harboring either sense or antisense sequences Large circular nucleic acid molecules that contain an antisense region specific to the target genes were constructed according to standard cloning procedure (Sambrook et al., *Molecular Cloning*, 1989). Competent bacterial cells (XL-1 Blue MRF') containing the pBS-KS (+) or (–) phagemid with the appropriate cDNA were infected with a helper bacteriophage M13K07 (NEB Nucleic Acids, USA). The orientation of the cloned cDNA in the phagemid vector determines either sense or antisense sequence. 20% polyethylene glycol (PEG 8000) was added to the supernatant of an overnight culture of helper phage infected cells grown in 2×YT The bacteriophage precipitate was resuspended in TE (pH 8.0), and phage genomic DNA was isolated with phenol extraction and ethanol precipitation.

(2) Purification of the Phage Genomic Antisense Molecules

Purification of phage genomic antisense molecules from the residual genomic DNA of Helper bacteriophage and host bacterial cells was carried out either with 0.8% low melting (LMP) agarose gel for small scale purification or with gel filtration column chromatography (1.0×50 cm) for large scale purification. The column resin for gel filtration was superfine Sephacryl™ S-1000 (molecular cutoff: 20,000 bp) (Amersham Pharmacia Biotech AB, Sweden), and was packaged and equilibrated with 50 mM Tris-HCl buffer containing 0.2 M NaCl (pH 8.3). The starting volume of the antisense molecules was adjusted to 5% of the gel void volume and DNA elution was carried out with the same buffer used for resin equilibration (flow rate: 0.3 ml/min). Samples were UV scanned at 260/280 nm with a dual UV detection system and were collected every 5 min during elution. Sample fractions were washed and precipitated with 70% cold ethanol and were resuspended in distilled ultrapure water and PBS (phosphate buffered saline) for subsequent experiments. The purified antisense molecules were tested for quantity and purity on a 1% agarose gel. Control sense molecules were constructed with the TNF-α cDNA fragment cloned in pBS-KS (+), in the opposite orientation of the lacZ gene in the vector. Single stranded molecules of either sense or antisense were confirmed for sequence integrity by employing the T7 primer for sequencing. DNA sequencing, was carried out with an automated DNA sequencer.

4. Structural Analysis and Stability Test of the Phage Genomic Circular Antisense Molecules The fact that the antisense molecules are single stranded, circular and stable was tested in the following manner. Antisense molecules (1 µg) to the gene encoding TNF-α were treated with XhoI (10 U/µg DNA), Exonuclease III (160 U/µg DNA), or S1 nuclease (10 U/µg DNA) at 37° C. for 3 hrs, and subjected to phenol extraction, ethanol precipitation and gel electrophoresis on a 1% agarose gel to study their stability as well as digestion patterns.

For the stability test, 1 µg of antisense molecules was tested alone or after complex formation with liposomes in a ratio of DNA: liposomes of about 1:3 (w/w). A not heat inactivated 30% FBS solution was added to the antisense-liposome complex and incubated at 37° C. for varying time periods for up to 48 hours. After incubation with FBS and the nucleases, antisense DNA was extracted with chloroform, precipitated with ethanol and run on a 1% agarose gel.

Thermal denaturation of the circular antisense molecules (TNF-α antisense) and double stranded plasmid DNA (pBS-KS(−) phagemid containing the TNF-α cDNA fragment) was performed in a solution of 100 mM NaCl, 10 mM MgCl$_2$ and 10 mM sodium PIPES (Sigma, USA). DNA at 10 µg/ml (10 nM) was heated to 95° C. and allowed to cool slowly to room temperature prior to denaturation experiments. The temperature was raised at a rate of 0.5° C./3 min. Melting studies were carried out in a diode array spectrophotometer equipped with a peltier temperature controller (Hewlett Packard, USA).

5. Detection of Target Gene Transcript (1) Transfection of Antisense Molecules Complexed with Liposomes Cationic liposomes, such as Lipofectamine™, Lipofectamine 2000™ or Lipofectamine Plus™ (Life Technologies, USA) were miked with either antisense molecules or sense control molecules. These liposome-DNA complexes were mixed with OPTI-MEM (Life Technologies, USA), and were then added to cells according to the protocol suggested by the manufacturer. Lipofection details are as follows: cells were cultured in PRMI 1640 or EMEM supplemented with 110% FBS and were washed twice with OPTI-MEM 30 minutes prior to lipofection. Cells were seeded on a 48-well plate ($1\times10^5$ cells/well) in 200 µl of culture media. Antisense molecules were mixed with cationic liposomes in a ratio of about 1:3 (w/w) and added to cells for transfection. Cells were incubated for 6 hrs at 37° C. in serum-free media. Following the lipofection, 2×FBS and antibiotics were added to the culture medium and incubated further for 18 hrs at 37° C. Rat TNF-α expression was induced with LPS (30 µg/ml). Cells were used for the preparation of RNA, and culture supernatant was tested for the presence of IL-10 with Enzyme Linked Immuno-Sorbent Assay (ELISA).

(2) Detection of Transcription with RT-PCR

RNA preparation was carried out with Tri reagent™ (MRC, USA) according to the protocol recommended by the manufacturer. Cells harvested from each well were mixed with 1 ml Tri Reagent and 200 µl chloroform for RNA purification. Purified RNA was subjected to RT-PCR in a 50 µl reaction volume by using the Access™ RT-PCR kit (Promega, USA). In a PCR tube was added purified RNA, a pair of primers (Table 2), AMV reverse transcriptase (5 U/µl), Tfl DNA polymerase (5 U/µl), dNTP (10 mM, 1 µl) and MgSO$_4$ (25 mM, 2.5 µl). Reverse transcription and polymerase chain reaction were sequentially carried out in a thermal cycler (Hybaid, UK). Synthesis of the first strand cDNA was carried out at 48° C. for 45 min and subsequent DNA amplification was carried out in 30 repetitive cycles, at 94 ° C. for 30 sec (denaturation), 59° C. for 1 min (annealing), and 68° C. for 2 min (polymerization). PCR product was confirmed on a 1% agarose gel, and quantitative analysis of the amplified DNA was performed with AlphaImager 1220, a gel documentation apparatus (Alpha Inno-Tech corporation, USA,).

(3) Southern Blotting

Probes for Southern hybridization were prepared with ECL (enhanced chemical luminescence) oligo-labeling and detection system (Amersham Life Science, UK). RT-PCR products were run on a 1% agarose gel and transferred onto a nylon membrane in 0.4 M NaOH solution. An oligonucleotide probe for TNF-α was a 22 mer: 5'-GATGAGAGGGAGC-CCATTTGGG-3' (SEQ ID NO:3), and an oligonucleotide probe for NF-κB was a 25 mer 5'-CTTCCAGTGCCCCCTC-CTCCACCGC-3' (SEQ ID NO:4).

Oliognucleotide probes of 100 pmol were mixed with fluorescein-11-dUTP, cacodylate buffer and terminal transferases, and were incubated at 37° C. for 70 min for ECL labeling. Probe hybridization to a nylon membrane with transferred DNA was carried out in a 6 ml hybridization buffer (5×SSC, 0.02% SDS, liquid block) at 42° C. for 14 hrs. The nylon membrane was washed twice in 5×SSC containing 0.1% SDS and once in 1×SSC containing 0.1% SDS, at 45° C. for 15 min for each washing. The membrane was incubated with an antibody conjugated to HRP anti-fluorescein for 30 min, followed by incubation with ECL detection reagent for about 5 min before exposure to an X-ray film.

(4) Detection of Polypeptides with ELISA or Western Blotting

Quantitation of target proteins after antisense treatment was examined with either ELISA or Western blotting method. For the ELISA assay, cell culture supernatant was diluted 50 fold and added to an ELISA plate coated with antibody against TNF-α. Biotinylated secondary antibody to anti TNF-α was added into each well of the ELISA plate and incubated at room temperature for 90 minutes. After three washings, streptavidin-peroxidase was added, and incubated for 45 minutes. The plate was washed four times to remove unbound streptavidin-peroxidase, and chromogen was added. After a 20 min incubation for color development, optical density was measured at 450 nm.

Western blotting was performed to examine the presence of CDK2. The amount of total proteins was determined with the BCA™ protein assay kit (Pierce, USA) after treating the cells with antisense or sense DNA. Twenty (20) μg protein samples were loaded onto a 12% polyacrylamide gel and electrophoresed. After gel electrophoresis, the proteins were transferred onto PVDF membrane (Bio-Rad, USA). The membrane was incubated for blocking with phosphate-buffered saline containing 3% non-fat milk and 0.05% Tween 20. The membrane was then incubated with rabbit polyclonal IgG antibody (Santa Cruz biotechnology, USA) to human CDK2. The secondary antibody of horseradish peroxidase-conjugated donkey anti-rabbit IgG (Amersham Life science, Sweden) was added, and protein bands were visualized using the ECL kit.

(5) MTT Assay to Determine Inhibition of Cell Growth

Antisense molecules to c-myb, k-ras and cdk2 were studied for their growth inhibitory effects using the MTT assay. The MTT reagent was (3-[4,5-Dimethylthiazol-2-yl]-2,5-diphenyl-tetrazolium bromide) (Sigma, USA). The K562, HL-60, HeLa and MCF-7 cells were washed twice with OPTI-MEM and seeded in each well of the 96-well plate in a 50 μl volume at a cell density of $6 \times 10^4$ cells/ml. Lipofectamine 2000 or Lipofectamine Plus (Life Technologies, USA) were complexed with antisense molecules in a ratio of about 1:3 (w/w) for cellular uptake. Cells were incubated with antisense-liposome complexes for 5 hr in OPTI-MEM containing 10% FBS (HyClone, USA) and maintained in a $CO_2$ (5%) incubator at 37° C. for 5 days.

MTT reagent was diluted with PBS to a concentration of 5 μg/ml, and 100 mg of the MTT reagent was added to each well containing 100 μl culture medium. Cells were maintained in a $CO_2$ (5%) incubator at 37° C. for 4 hr and treated with an equal amount of isopropanol (containing 0.1 N HCl) at room temperature for 1 hr. The cells were then measured for absorbance at 570 nm with an ELISA reader, SpectraMAX 190 (Molecular devices, USA).

Example 2

Experimental Methods and Results

Figure 2:
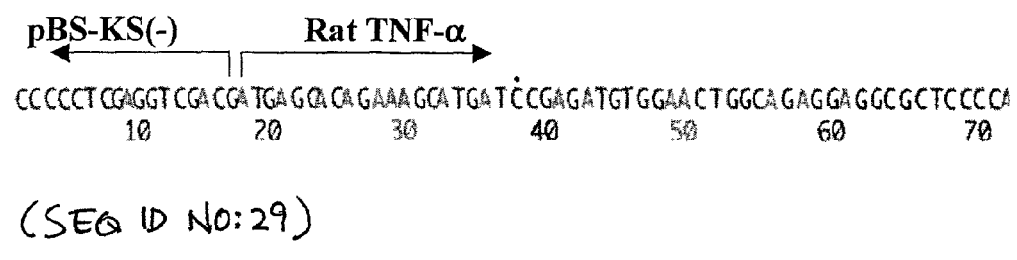
FIG. 2 shows DNA sequence of TNFα-M13kS. DNA sequencing was performed to confirm the presence of TNF-α antisense sequence in TNFα-M13AS using the T3 sequencing primer. The sense sequence is shown for TNF-α, and is shown under the arrow pointing to the right. The actual antisense sequence of the template is reversed and complementary.

1. Construction of Large Circular Nucleic Acid Compound Using the Recombinant M13 Bacteriophage System Experiments were carried to determine whether the circular phage genome of M13 bacteriophages (phage) can harbor an antisense sequence as a part of its genome and whether these new antisense molecules can overcome the problems associated with synthesized forms of antisense oligonucleotides. Production of recombinant M13 phage was carried out by infecting M13K07 helper phages into bacterial cells that were already transformed with pBluescript KS (−) phagemid (Jupin et al. *Nucleic Acid Res.*, 23, 535-536 (1995)). We utilized the F1 origin of the phagemid to generate single stranded circular phage genome containing either antisense or sense sequence for a target gene. In the case of the genie encoding rat TNFα, the entire cDNA of the gene was placed into pBluescript KS (−) vector to produce the antisense sequence (FIG. 1). The antisense sequence in the single stranded genomic DNA was confirmed by DNA sequencing using T7 sequencing primers (FIG. 2). Both the 5' and 3' flanking sequences of the TNF-α antisense insert were shown to be those of the phagemid vector. The insert sequence corresponded with that of TNF-α mRNA, demonstrating that the antisense sequence was present. The circular phage genome containing the antisense sequence for TNF-α, NF-kB, c-myb, c-myc, k-ras and cdk2 were designated as TNFα-M13AS, NFκB-M13AS, c-myb-M13AS, c-myc-M13AS, k-ras-M13AS, and cdk2-M13AS, respectively.

2. Column Chromatographic Purification of Phage Genomic Antisense DNA

TNFα-M13AS was isolated after infecting bacterial cells that were already transformed with recombinant phagemid harboring rat TNF-α cDNA with M13K07 helper phages. When phage genomic DNA with an antisense sequence is produced using the phagemid system, the single stranded DNA can be contaminated with a minor amount of the double stranded replication form of M13 phage and/or wild type single stranded genomic DNA from helper phages. In addition, antisense preparation was found to contain a high level of contaminated lipopolysaccharides (LPS) that significantly lowered transfection efficiency and affected cell proliferation (data not shown). Phage genomic DNA containing the antisense sequence may be isolated in small amounts by using an agarose gel purification method.

Figure 3:
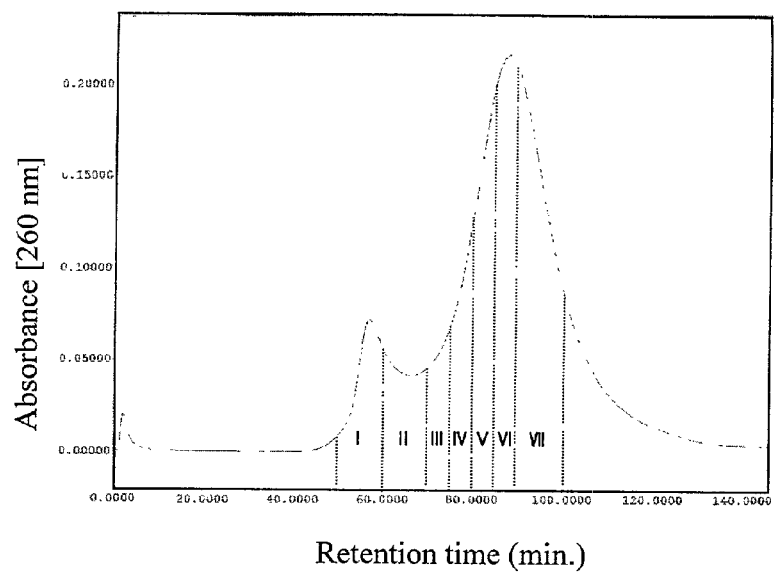
FIGS. 3A and 3B show chromatographic purification of phage genomic antisense molecules. A. Elution profiles for the circular antisense molecules from gel filtration column chromatography. Sephacryl S-1000 superfine (1.0×50 cm) resin was employed for DNA fractionation. Elution buffer was 50, mM Tris-HCl (pH 8.3) containing 0.2 M NaCl and flow rate was set at 0.3 ml/min. Sample volume for each faction was set at 70 μg (70 μl of 1 mg/ml). B. Electrophoretic patterns of fractions obtained from gel filtration column chromatography. Lane 1, crude DNA; and lanes 2-8, fractions I-VII corresponding to retention times. Purified DNA was run on a 1% agarose gel and visualized with ethidium bromide staining.
Figure 3:
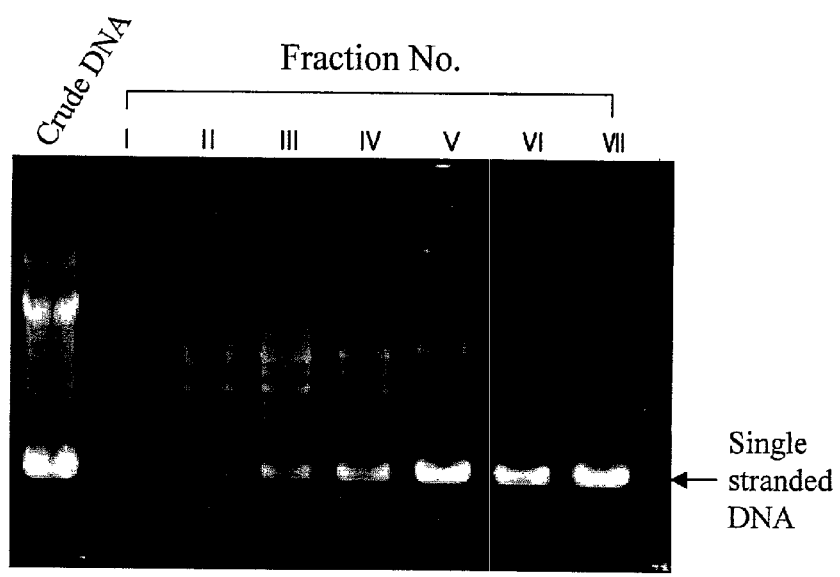

Gel filtration column chromatography was tested for large-scale purification of the circular phage genomic antisense DNA. Sephacryl S-1000 superfine gel was equilibrated with 50 mM Tris-HCl buffer (pH 8.3, 0.2 M NaCl) and was loaded with the antisense sample (5% of the gel volume). When the column was eluted with the elution buffer, which was the same as the equilibration buffer, a major peak was obtained from the retention time of 75 to 120 min (FIG. 3A). Peaks were divided into 7 fractions by 5 or 10 min retention time for each fraction, from fractions I to VII. Each eluate fraction was loaded on 1% agarose gel to confirm purification quality of the antisense strand (FIG. 3B). Wild type M13 bacteriophage DNA was found in fraction III as a major band (75 min retention time). Fraction IV contained the large circular antisense molecule as a major band (80 min retention time). Fractions spanning from 80 to 10 min retention time were pooled and precipitated with ethanol. Antisense precipitate was then washed with 70% cold ethanol and resuspended in distilled water for further experiments. The large circular antisense strand was obtained at a 60% recovery rate and the optical density of the antisense was above 1.8 at the 260/280 ratio. When measured for LPS with the LAL test, the antisense molecules were largely free of LPS contamination, demonstrating efficient removal of contaminants by chromatographic purification.

3. Structural Analysis and Stability Test of Phage Genomic Antisense DNA

Figure 4:
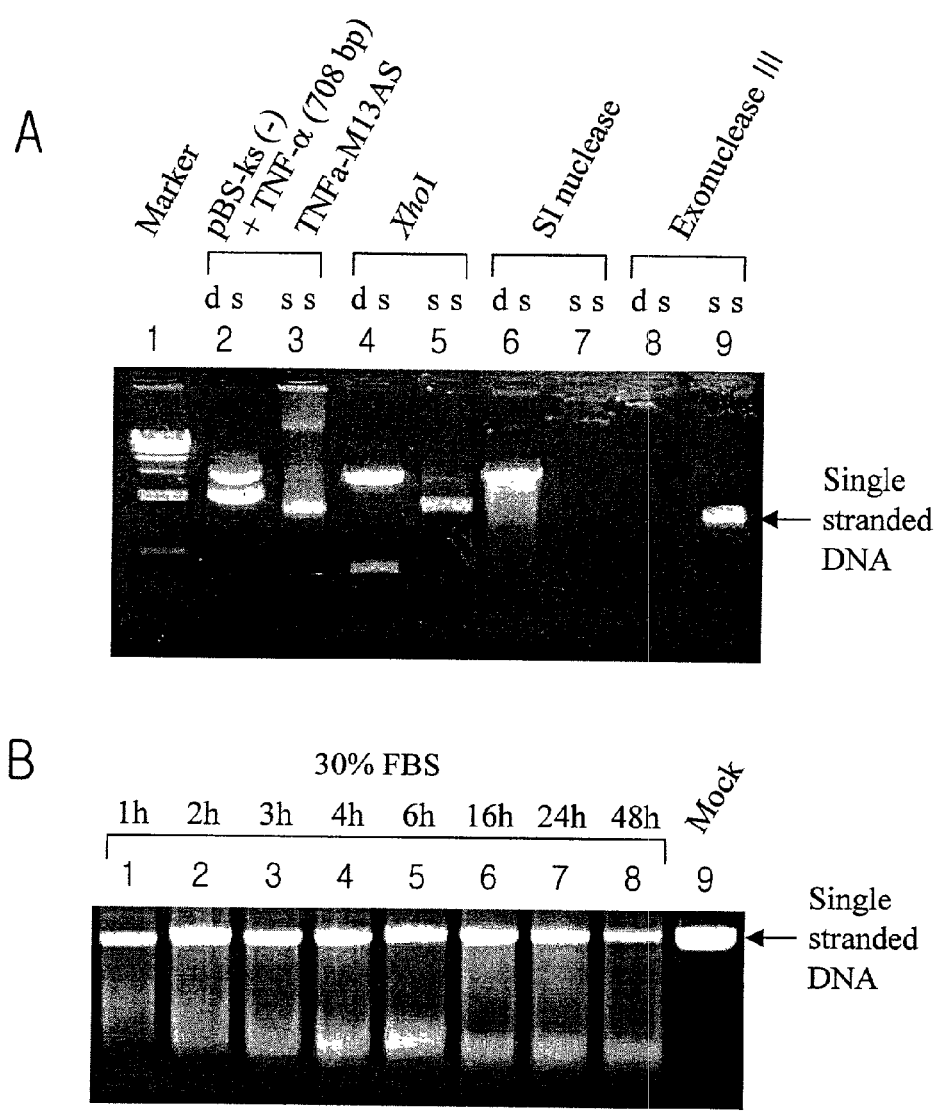
FIGS. 4A and 4B show biochemical properties of phage genomic antisense molecules containing the TNF-α sequence. A. Characterization of TNFα-M13AS molecules. Lane 1, lambda HindIII DNA size marker; lane 2, plasmid DNA containing the TNFα cDNA (TNFα-plasmid); lane 3, TNFα-M13AS; lane 4, TNFα-plasmid digested with Xho I; lane 5, TNFα-M13AS digested with Xho I; lane 6, TNFα-plasmid digested with S1 nuclease; lane 7, TNFα-M13AS digested with S1 nuclease; lane 8, TNFα-plasmid digested with Xho I was then incubated with exonuclease III; and lane 9, TNFα-M13AS digested with Xho I was then incubated with exonuclease III. TNFα-plasmid or TNFα-M13AS was incubated with various enzymes as specified by the manufacturer. B. Stability test of TNFα-M13AS. The phage genomic antisense molecules were incubated for various periods of time in 30% fetal bovine serum. Lanes 1-8, treated with sera for different periods of time; and lane 9, sham treated control. Antisense molecules treated with sera were run on a 1% agarose gel and visualized with ethidium bromide staining.

TNFα-M13AS was tested for its circular structure and stability to nucleases. The antisense molecules were expected to be stable to exonucleases because of their closed circular structure. When TNFα-M13AS was incubated with the endonuclease XhoI and exonuclease III, the antisense molecules were found to be largely intact even after a 3 hr incubation with the nucleases. In contrast, when XhoI was added to the double stranded replication form of the recombinant M13 phage DNA, the DNA was, as expected, completely digested by the combination of the restriction enzyme and exonuclease III. The fact that TNFα-M13AS was a single stranded circular molecule was confirmed by the complete digestion of the antisense molecules with S1 nuclease (FIG. 4A).

Phage genomic antisense molecules were also found to be stable since their structural integrity was largely preserved after incubation with serum. When TNFα-M13AS was combined with cationic liposomes, a large fraction of the antisense molecules remained intact after extended incubation in fetal bovine serum (FBS). In fact, TNFα-M13AS remained intact even after 24 hr incubation with 30% FBS. The results suggest that the phage genomic antisense molecules may be further stabilized during in vivo application by forming complexes with liposomes (FIG. 4B).

Figure 5:
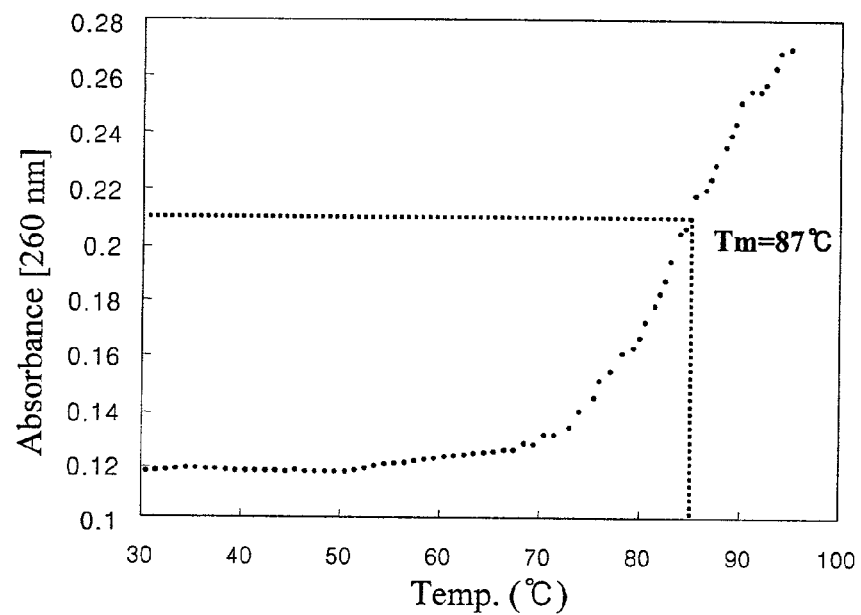
FIGS. 5A and 5B show melting temperature profiles for TNFα-M13AS and double stranded plasmid molecules. Absorbance was monitored at every 0.5° C. increment in 3 min intervals while temperature was raised from 30° C. to 95° C. A. Tm1/2 profile of double stranded phagemid containing the TNFα insert. B. Tm1/2 profile of TNFα-M13AS, single stranded circular antisense molecules.
Figure 5:
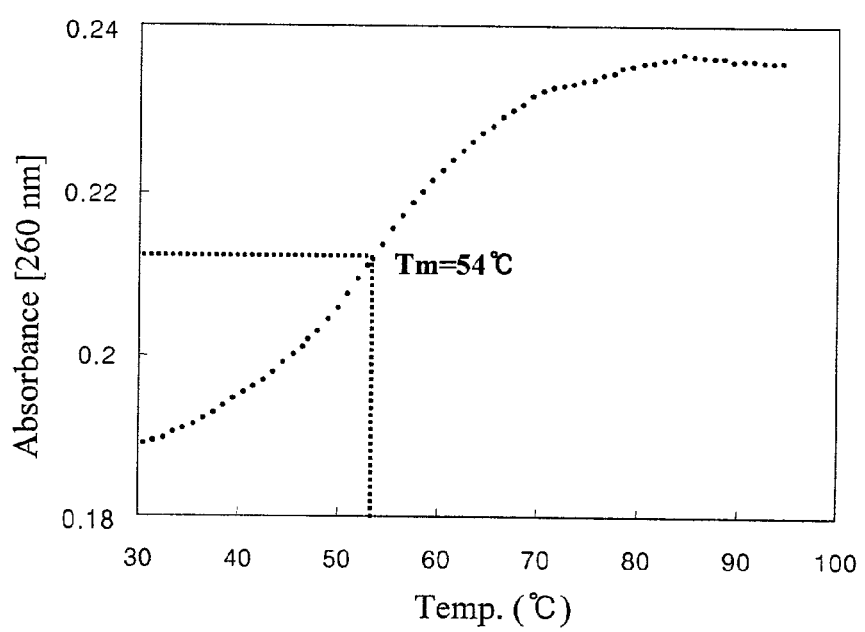

The structural difference between the single stranded TNFα-M13AS and the double stranded phagemid DNA containing TNF-α insert was also examined by measuring the melting temperature (Tm1/2). When absorbance at 260 nm was monitored for double stranded phagemid DNA when the temperature was raised progressively, a typical chromatic change was detected at around 87° C. However, when the phage genomic antisense molecules were examined for their melting temperature, the chromatic change of a mild slope was detected at around 54° C., indicating that regions with short intra-molecular duplexes were denatured (FIG. 5). These results confirm that TNFα-M13AS is a single stranded and circular molecule.

4. Effective and Specific Elimination of Rat TNF-α mRNA by TNFα-M13AS

The antisense activity of TNFα-M13AS was tested. TNFα-M13AS contains a long antisense sequence that includes nonspecific antisense phagemid vector sequences and an antisense region specific to rat TNFα mRNA. The fact that the phage genomic antisense molecules have a large amount of nonspecific sequences necessitates a thorough analysis of target specificity of the antisense activity. In order to determine whether phage genomic antisense molecules act specifically to eliminate target gene expression, multiple control genes were used to compare levels of mRNA ablation.

Figure 6:
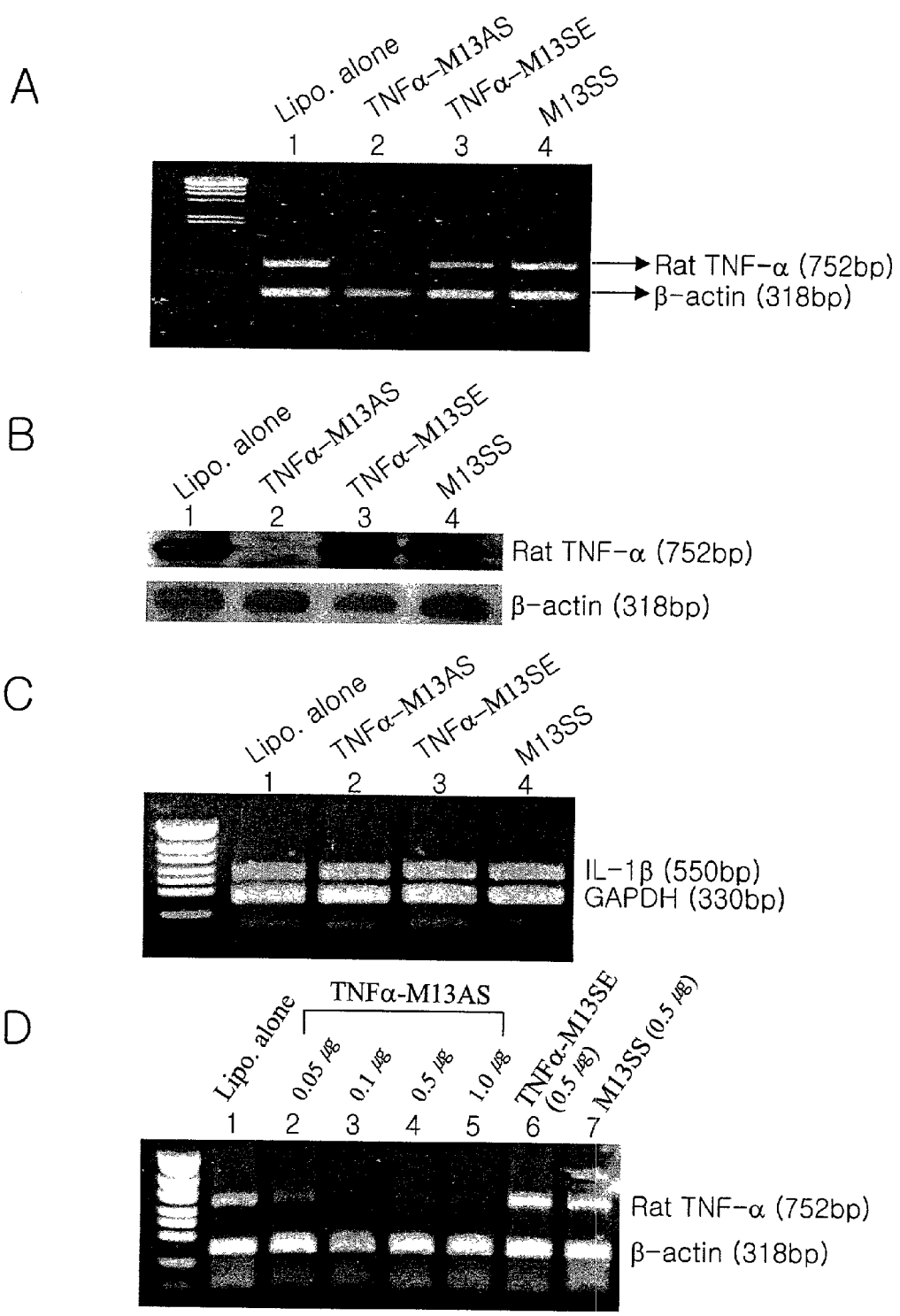
FIGS. 6A-6D show antisense activity of TNFα-M13AS on TNFα mRNA level in WRT7/P2 cells. Results shown in A, C and D were obtained from RT-PCR, and the results shown in B were obtained from Southern hybridization. RT-PCR was performed with total RNA. Cells were treated with TNFα-M13AS (1.4 nM, 1.65 μg/ml) complexed with Lipofectamine (6.6 μg/ml). After lipofection of the antisense molecules, TNF-α was induced with LPS treatment in WRT7/P2 cells and total RNA was then isolated. A. RT-PCR was performed with 2 sets of primers, either TNF-α primers or β-actin primers: Lane 1, liposomes alone; lane 2, TNFα-M13AS (antisense); lane 3, TNFα-M13SE (sense); and lane 4, M13SS (phage genomic DNA without an antisense insert). B. DNA from panel A was transferred to a nylon membrane and probed with labeled 20 mer oligonucleotides. C. IL-1β and GAPDH were amplified by RT-PCR to examine non-specific antisense effects. The amounts of total RNA and single stranded circular molecules, including the antisense compounds were the same as those in panel A. Amplified PCR fragments were run on a 1% agarose gel and visualized with ethidium bromide staining. D. Dose dependent effects of TNFα-M13AS on TNFα mRNA expression. Lane 1, liposome alone; lanes 2-5, TNFα-M13AS; lane 6, TNFα-M13SE; and lane 7, M13SS.

To test the specific activity of TNFα-M13AS, 0.5 µg (1.4 nM) of the antisense molecules were complexed with 1.5 µg of cationic liposome and were added to $1 \times 10^5$ cells of a monocytic cell line, WRT7/P2. The cells were then induced for TNF-α expression by LPS treatment. When the cells were treated with TNFα-M13AS, the induction level of TNF-α mRNA was significantly reduced. In contrast, when cells were treated with either TNFα-M13SE (the sense strand of TNF-α) or M13SS (single stranded phage genome without the antisense insert) they did not show much reduction of TNF-α mRNA (FIG. 6A). RT-PCR band of TNF-α was confirmed by Southern hybridization using a probe that binds to the middle of the amplified DNA fragments (FIG. 6B).

TNFα-M13AS contains the rat TNF-α antisense sequence as well as antisense sequences of the β-galactosidase (LacZ) and the lactamase (Amp) genes, harboring a total of 3.7 kb single stranded circular genome. The TNF-α specific antisense portion is about 708 bases long. Thus, the TNF-α specific antisense sequence in TNFα-M13AS is itself very long when compared with conventional synthetic antisense molecules of some 20 or 30 nucleotides. This is significant because it has been generally believed in the art that as the antisense molecule is lengthened, its sequence specificity declines. Further confirming tests were carried out to show that the antisense activity of TNFα-M13AS is indeed sequence specific.

In order to demonstrate sequence specific antisense activity, three different genes were examined for mRNA levels after lipofection of TNFα-M13AS. These were β-actin, GAPDH (glyceraldehyde 3-phosphate dehydrogenase), and IL-1,β (interleukin-1 β). Expression of these genes was not affected by lipofection of TNFα-M13AS (FIG. 6A,C).

Dose response of TNFα-M13AS in its antisense activity was also examined. When TNFα-M13AS was used at a concentration of 0.01 µg (0.03 nM), TNF-α expression was only slightly reduced. At a concentration of 0.05 µg (0.14 nM), TNF-α expression was partially eliminated. When the amount of TNFα-M13AS was increased to 0.1 µg (0.28 nM), TNF-α mRNA was found to be completely abolished (FIG. 6D). These results show that TNFα-M13AS is effective for the elimination of target mRNA using a much smaller amount than conventionally used antisense molecules.

Figure 7:
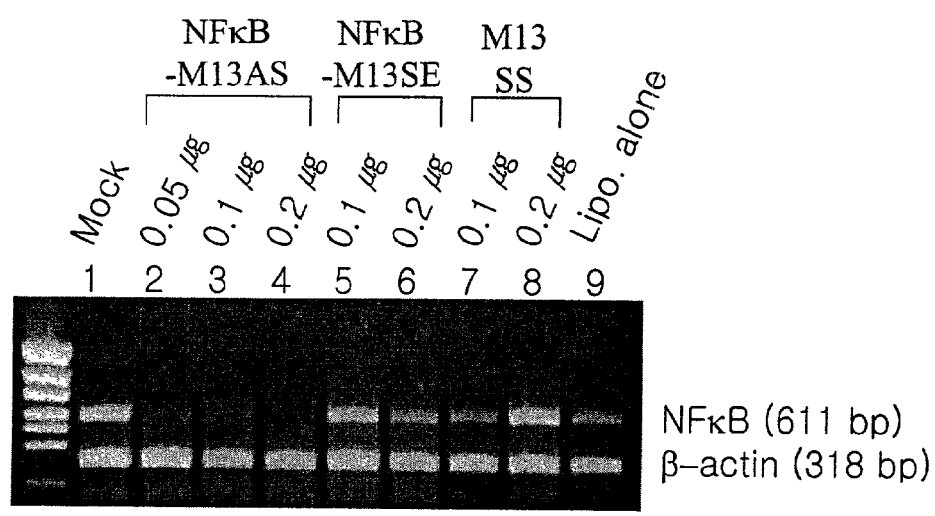
FIGS. 7A and 7B show the effects of NFκB-M13AS on human NF-κB mRNA levels in THP1 cells. THP1 cells (1×10⁵ cells/well) were transfected with different amounts of NFκB-M13AS, NFκB-M13SE, or M13SS. After lipofection, cells were stimulated with PMA (160 nM) for 6 hours. Total RNA was isolated and subjected to RT-PCR. A. messenger RNA levels of NF-κB were reduced by NFκB-M13AS treatment in a dose dependent manner. According to the figure, unlabeled lane to the left of lane 1 is a molecular weight marker (100 bp ladder marker), Lane 1, sham treated control; lanes 2-4, NFκB-M13AS (0.14 nM, 0.28 nM and 0.56 nM, respectively); lanes 5-6, NFκB-M13SE (0.28 nM and 0.56 nM, respectively); lanes 7-8, M13SS (0.28 nM and 0.56 nM); and the unlabeled lane to the right of lane 9 is Lipofectamine alone. B. DNA bands in the panel A were transferred onto a nylon membrane and subjected to Southern hybridization.
Figure 7:
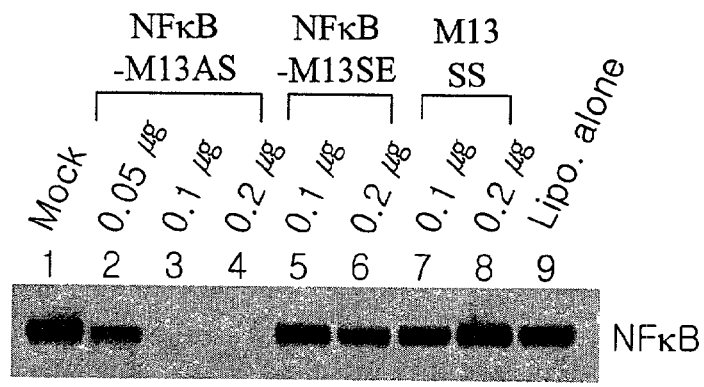

5. Specific Elimination of mRNA Expression by Phage Genomic Antisense Molecules to the NF-κB, c-myc, c-myb, k-ras and cdk2 Genes Observing the effectiveness of TNFα-M13AS, experiments were carried out to determine whether phage genomic antisense compounds specifically directed to other genes block the expression of these other genes, such as NF-κB, c-myc, c-myb, k-ras and cdk2. Antisense compound to NF-κB (NFκB-M13AS) was produced and tested in THP-1 cells for efficient antisense activity. NFκB-M13AS was also complexed with liposomes and was added to the cells in increasing amounts. When 0.05 µg (0.14 nM) of NFκB-M13AS was added to THP-1, NF-κB mRNA was reduced by about 70%. When the amount of NFκB-M13AS was increased to 0.1 g (0.28 nM) and to 0.2 µg (0.56 nM), NF-κB mRNA was eliminated by more than 90%. In contrast, cells that were treated with either NFκB-M13SE (phage genomic DNA with the sense sequence of NFκB) or with M13SS, NF-κB expression was not much affected (FIG. 7A). PCR amplified bands of NF-κB were further authenticated by Southern hybridization (FIG. 7B).

Figure 8:
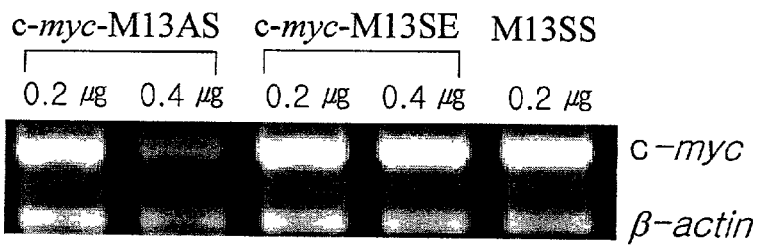
Figure 8:
Figure 8:
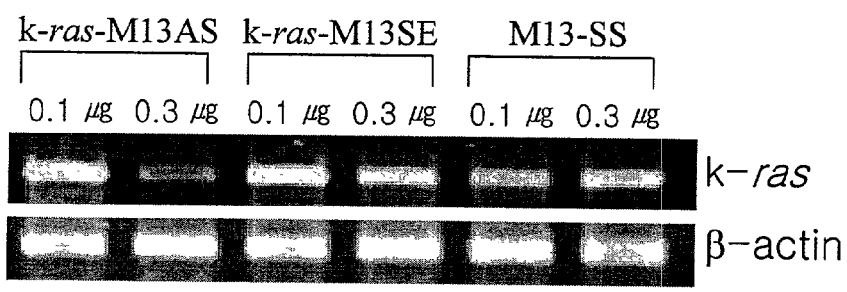
Figure 8:
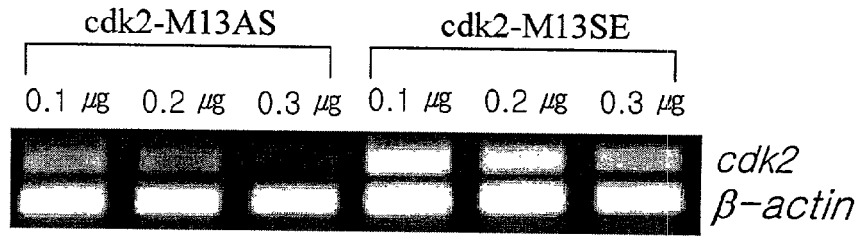

When 0.4 µg (1.12 nM) of c-myc-M13AS was added to K562 cells, c-myc mRNA was reduced by about 80%. In contrast, in K562 cells that were treated with either c-myc-M13SE or M13SS, c-myc expression was substantially not affected. (FIG. 8A). When 0.2 µg (0.56 nM) and 0.4 µg (1.12 nM) of c-myb-M13AS were added to HL-60 cells, c-myb mRNA was reduced by about 70% compared with c-myb-M13SE. In contrast, in HL-60 cells that were treated with c-myb-M13SE expression was substantially not affected (FIG. 8B).

When 0.3 µg (0.84 nM) of k-ras-M13AS was added to HeLa cells, k-ras mRNA was reduced by about 80%. In contrast, in HeLa cells that were treated with either k-ras-M13 SE or with M13SS, k-ras expression was not much affected (FIG. 8C).

Finally, when 0.1 µg (0.28 nM) and 0.2 µg (0.56 nM) of cdk2-M13AS were added to HeLa cells, cdk2 mRNA level was reduced by about 70% and 75%, respectively in comparison with cdk2-M13SE. When the amount of cdk2-M13AS was increased to 0.3 µg (0.84 nM), endogenous cdk2 mRNA level was eliminated by more than 90%. In contrast, in HeLa cells that were treated with cdk2-M13SE, cdk2 expression was not substantially affected (FIG. 8D).

6. Reduction in TNF-α and CDK2 Activity

When mRNA of a target gene is eliminated through antisense methods, the translational products of the mRNA cannot be made. Confirmation of reduced or ablated proteins of a target gene is thus necessary to support the biological effect caused by antisense molecules. Protein levels were examined in two different ways after treating cells with antisense molecules.

WRT7/P2 cells were lipofected with TNFα-M13AS, and TNF-α secreted from the transfectants was measured using the ELISA assay. Similar to the level of reduction of endogenous TNF-α mRNA, TNF-α protein in the cell culture supernatant was also reduced by more than 90% after administering TNFα-M13AS (FIG. 9A). However, neither of the control antisense molecules, TNFα-M13SE (containing the sense strand of the TNF-α gene) or M13SS, reduced TNF-α expression in WRT7/P2 transfectants. These results demonstrate that TNFα-M13AS was effective in both the elimination of TNF-α mRNA and subsequent disappearance of TNF-α from the transfectants.

CDK2 level in the transfectants of cdk2-M13AS was examined by Western blotting. HeLa cells were treated with either cdk2-M13AS, or cdk2-M13SE, and the cells were then used for extraction of total cellular proteins; 48 hrs after transfection. Isolated proteins were normalized for quantity and assayed using Western blotting technique. Whereas cdk2-M13AS at a concentration of 0.8 nM (0.3 µg/well) reduced the CDK2 level by more than 70%, cdk2-M13SE had no effect on the cellular level of the protein (FIG. 9B). These results demonstrate that this phage genomic antisense molecule functions effectively in the specific elimination of target mRNA, which in turn leads to the disappearance of the target proteins in the transfectants.

7. Growth Inhibition of Cancer Cells by the Phage Genomic Antisense Method

Oncogenes are involved in neoplastic transformation and progression of cancer cells. Since oncogenes are good targets for antisense intervention, several tumor cell lines were tested to determine whether growth inhibition occurs if expression of two important oncogenes, c-myb and k-ras are specifically blocked by phage genomic antisense molecules specific to these genes. In addition, since cdk2 gene expression was blocked in response to administration of cdk2-M13AS, its inhibitive effect on tumor cell growth was also examined.

Figure 10:
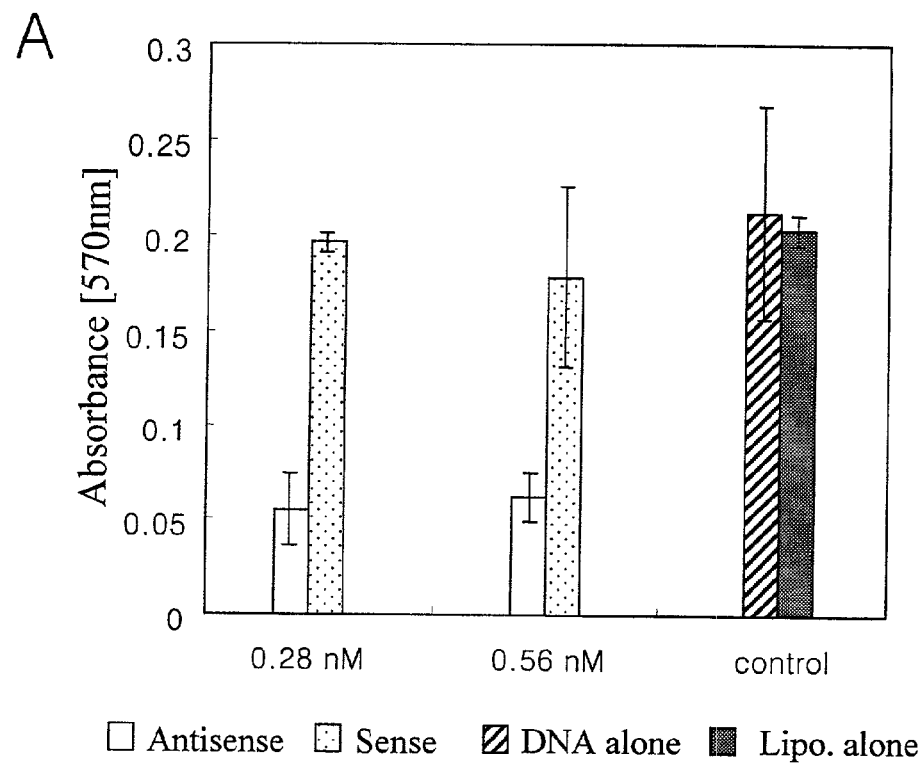
Figure 10:
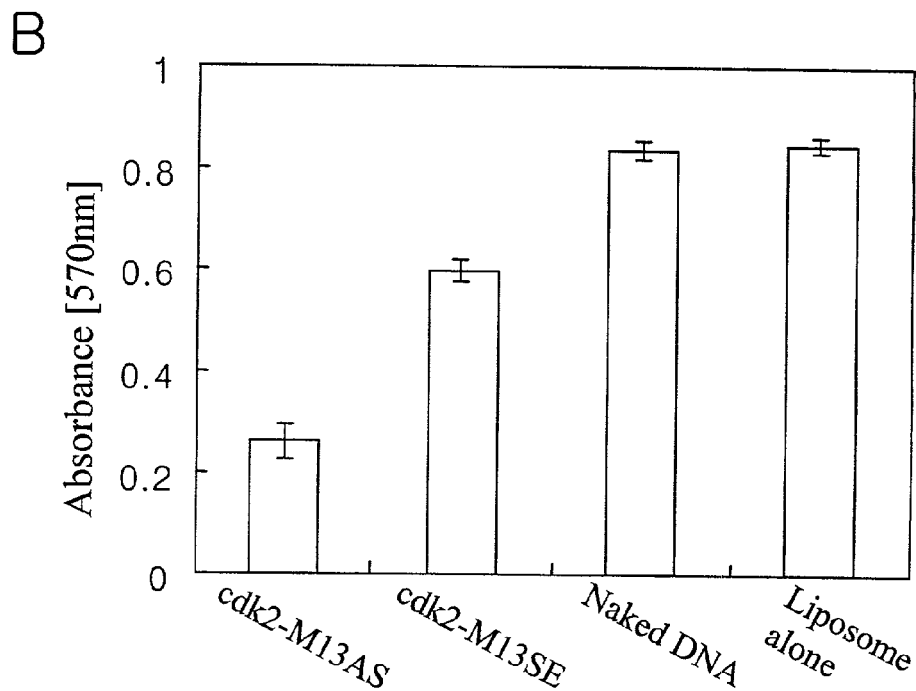
Figure 11:
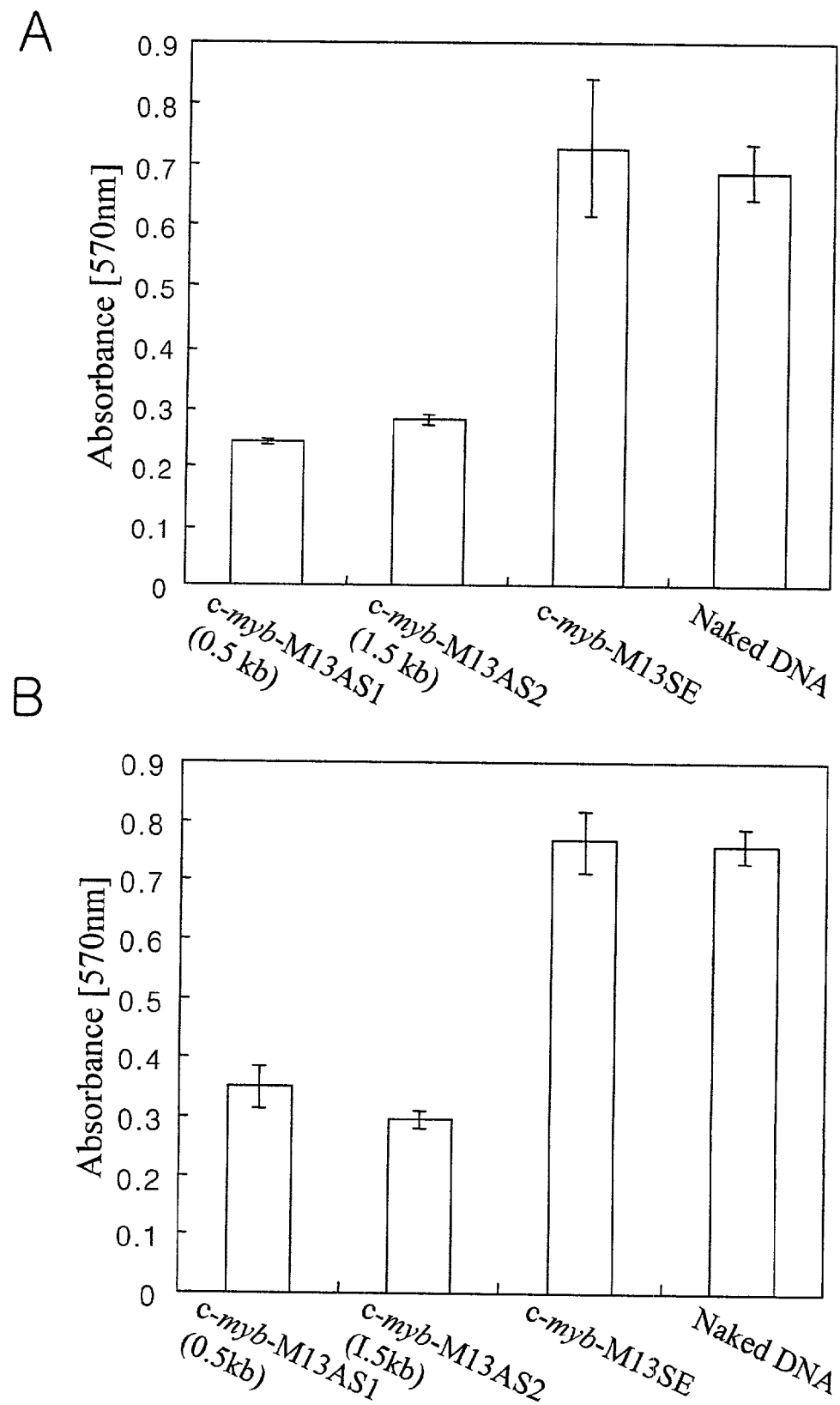

Phage genomic antisense molecule to k-ras was added to MCF-7 (breast cancer) cell lines; antisense molecule to c-myb was added to either K562 (chronic myelogenous leukemia) or HL-60 (acute promyelocytic leukemia) cell line; and antisense molecule to cdk2 was added to HeLa (cervical cancer) cell line. The antisense transfectants for each of these antisense compounds were then examined for inhibition of tumor cell growth using the MTT assay (FIGS. 10 and 11).

When the phage genomic antisense molecule to k-ras (k-ras-M13AS) was added to MCF-7 cells, the transfectants exhibited more than 70% inhibition in cell growth at antisense concentrations of both 0.1 µg (0.5 nM) and 0.2 µg (1 nM). In contrast, k-ras-M13SE (the sense control of the Ras gene) revealed only marginal inhibition of cell growth, less than about 9% inhibition at 0.5 nM antisense concentration, and less than about 15% at 1 µM concentration (FIG. 10 A).

When HeLa cells were treated with cdk2-M13AS at a concentration of 2 nM, more than 70% growth inhibition was observed. In contrast, cdk2-M13SE (the sense control of the cdk2 gene) exhibited less than 30% growth inhibition of the transfected HeLa cells (FIG. 10B).

Antisense molecules to c-myb were constructed in two different lengths, 0.5kb (c-myb-M13AS1) and 1.5kb (k-myb-M13AS2). When leukemic cell lines, K562 and HL-60, were treated with either c-myb-M13AS1 or c-myb-M13AS2, growth inhibition of these cell lines were observed to be similar at more than about 60% growth inhibition (FIG. 11). In contrast, c-myb-M13SE (control sense molecules) showed no substantial growth inhibition of K562 and HL-60 cells.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

TABLE 1

List of Cloning Primers and Size

| Primer | | Sequences | | Clone size (bp) |
|---|---|---|---|---|
| c-myb1 | 5' | 5'-ggcggcagcgccctgccgacgcc-3' | (SEQ ID NO:5) | 502 |
|  | 3' | 5'-cattgttttccaattctcccct-3' | (SEQ ID NO:6) |  |
| c-myb2 | 5' | 5'-cggcggagccccgccgcccgccgc-3' | (SEQ ID NO:7) | 1560 |
|  | 3' | 5'-tgaaactcagcaacaaatccag-3' | (SEQ ID NO:8) |  |
| c-myc | 5' | 5'-ggagaacttctaccagca-3' | (SEQ ID NO:9) | 978 |
|  | 3' | 5'-gacattctcctcggtgtccgaggac-3' | (SEQ ID NO:10) |  |
| k-ras | 5' | 5'-cggactgggagcgagcgcggcgcag-3' | (SEQ ID NO:11) | 761 |
|  | 3' | 5'-gaaaaaaattaggtaatgctaaaa-3' | (SEQ ID NO: 12) |  |
| cdk2 | 5' | 5'-atggctacctctcgatatga-3' | (SEQ ID NO:13) | 911 |
|  | 3' | 5'-cactccggattaccttcat-3' | (SEQ ID NO:14) |  |
| NFκB | 5' | 5'-gatcgtcgacgcgccacccggcttcagaatggc-3' | (SEQ ID NO:15) | 700 |
|  | 3' | 5'-gatcgaattcggtgaagctgccagtgctatccg-3' | (SEQ ID NO:16) |  |

TABLE 2

List of RT-PCR Primers

| Gene | Primer | Sequences | |
|---|---|---|---|
| TNF-α | 5'primer | 5'-catctccctccggaaaggacac-3' | (SEQ ID NO:17) |
| | 3'primer | 5'-cggatgaacacgccagtcgc-3' | (SEQ ID NO:18) |
| NFκB | 5'primer | 5'-cctggccggagccactagac-3' | (SEQ ID NO:19) |
| | 3'primer | 5'-ctatactcagatccatcacc-3' | (SEQ ID NO:20) |
| c-myc | 5'primer | 5'-ccagcagcctcccgcgacgatg-3' | (SEQ ID NO:21) |
| | 3'primer | 5'-gaggggtcgatgcactctgagg-3' | (SEQ ID NO:22) |
| c-myb | 5'primer | 5'-gctaccaacacagaaccacac-3' | (SEQ ID NO:23) |
| | 3'primer | 5'-tgaaactcagcaacaaatccag-3' | (SEQ ID NO:24) |
| k-ras | 5'primer | 5'-ctcccggcccccgccatttc-3' | (SEQ ID NO:25) |
| | 3'primer | 5'-ctctgggaatactggcacttcg-3' | (SEQ ID NO:26) |
| cdk2 | 5'primer | 5'-ctgacccgactcgctggcgc-3' | (SEQ ID NO:27) |
| | 3'primer | 5'-ggagagggtgagattagggc-3' | (SEQ ID NO:28) |

---

What is claimed is:

1. A method for inhibiting expression of a protein by a large circular single-stranded nucleic acid molecule targeted to an RNA encoding the protein comprising contacting a cell expressing the protein with a composition comprising:
   (i) a large circular single-stranded nucleic acid molecule comprising at least one target gene-specific antisense region, wherein said large circular single-stranded nucleic acid molecule is effective for reducing expression of said gene, wherein said molecule comprises a recombinant bacteriophage or phagemid genome; and
   (ii) a transfection effective carrier thereof comprising a lipid.

2. The method according to claim 1, wherein expression of said target protein causes cell proliferation or cancer.

3. The method according to claim 2, wherein said cancer is leukemia, lung cancer, liver cancer, colon cancer, stomach cancer, pancreatic cancer, brain cancer or prostate malignancy.

4. The method according to claim 3, wherein said cancer is leukemia, cervical cancer, or breast cancer.

5. The method according to claim 2, wherein said target protein is tumor necrosis factor, nuclear factor, MYB, MYC, RAS, or cell division kinase.

6. The method according to claim 1, wherein said protein is a viral protein.

7. The method according to claim 6, wherein said virus is herpes, human papilloma virus (HPV), HIV, small pox, mononucleosis (Epstein-Barr virus), hepatitis, or respiratory syncytial virus (RSV).

8. The method according to claim 1, wherein expression of said target protein causes a metabolic disease or an immunological disorder.

9. A method for inhibiting expression of a plurality of proteins comprising contacting a cell expressing the proteins with a composition comprising:
   (i) a large circular single-stranded nucleic acid molecule comprising at least one target gene-specific antisense region, wherein said large circular single-stranded nucleic acid molecule is effective for reducing expression of said gene, wherein said molecule comprises a recombinant bacteriophage or phagemid genome; and
   (ii) a transfection effective carrier thereof comprising a lipid.

10. A method for inhibiting cell proliferation, comprising, administering to said cell a composition comprising:
    (i) a large circular single-stranded nucleic acid molecule comprising at least one target gene-specific antisense region, wherein said large circular single-stranded nucleic acid molecule is effective for reducing expression of said gene, wherein said molecule is at least about 3,000 nucleotides long; and
    (ii) a transfection effective carrier thereof comprising a lipid, in which inhibiting expression of a target gene or genes inhibits cell proliferation.

11. The method according to claim 10, wherein the antisense region of the molecule is at least about 50 nucleotides long.

12. The method according to claim 10, wherein the antisense region is complementary to an entire gene sequence.

13. The method according to claim 10, wherein the nucleic acid molecule is a single stranded recombinant bacteriophage or phagemid genome.

14. The method according to claim 13, wherein said bacteriophage or phagemid is a filamentous phage.

15. The method according to claim 14, wherein the filamentous phage is phage M13.

16. The method according to claim 1, wherein the antisense region of the molecule is at least about 50 nucleotides long.

17. The method according to claim 1, wherein the antisense region is complementary to an entire gene sequence.

18. The method according to claim 1, wherein the molecule is at least about 3,000 nucleotides long.

19. A method for inhibiting expression of a protein by a large circular single-stranded nucleic acid molecule targeted to an RNA encoding the selected protein comprising contacting a cell expressing the protein with a composition comprising:
    (i) a large circular single-stranded nucleic acid molecule comprising at least one target gene-specific antisense region, wherein said large circular single-stranded nucleic acid molecule is effective for reducing expression of said gene, wherein said molecule is at least about 3,000 nucleotides long; and
    (ii) a transfection effective carrier thereof comprising a lipid.

20. The method according to claim 10, wherein the lipid is a liposome.

21. The method according to claim 1, wherein the lipid is a liposome.

22. The method according to claim 10, wherein the lipid is a cationic lipid.

23. The method according to claim 1, wherein the lipid is a cationic lipid.

24. The method according to claim 10, wherein the nucleic acid is DNA.

25. The method according to claim 1, wherein the nucleic acid is DNA.

26. The method according to claim 1, wherein the contacting of the cell with the composition occurs in vitro.

27. The method according to claim 9, wherein the contacting of the cell with the composition occurs in vitro.

28. The method according to claim 10, wherein the inhibiting of cell proliferation occurs in vitro.

29. The method according to claim 19, wherein the contacting of the cell with the composition occurs in vitro.

* * * * *

SEQUENCE LISTING

<160> NUMBER OF SEQ ID NOS: 29

<210> SEQ ID NO 1
<211> LENGTH: 33
<212> TYPE: DNA
<213> ORGANISM: Artificial Sequence
<220> FEATURE:
<223> OTHER INFORMATION: Artificial Sequence: Synthetic Primer

<400> SEQUENCE: 1
gatcgtcgac gatgagcaca gaaagcatga tcc                33

<210> SEQ ID NO 2
<211> LENGTH: 33
<212> TYPE: DNA
<213> ORGANISM: Artificial Sequence
<220> FEATURE:
<223> OTHER INFORMATION: Artificial Sequence: Synthetic Primer

<400> SEQUENCE: 2
gatcgaattc gtcacagagc aatgactcca aag                33

<210> SEQ ID NO 3
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 3
gatgagaggg agcccatttg gg                22

<210> SEQ ID NO 4
<211> LENGTH: 25
<212> TYPE: DNA
<213> ORGANISM: Artificial Sequence
<220> FEATURE:
<223> OTHER INFORMATION: Artificial Sequence: Synthetic Primer

<400> SEQUENCE: 4
cttccagtgc cccctcctcc accgc                25

```
<210> SEQ ID NO 5
<211> LENGTH: 23
<212> TYPE: DNA
<213> ORGANISM: Artificial Sequence
<220> FEATURE:
<223> OTHER INFORMATION: Artificial Sequence: Synthetic Primer

<400> SEQUENCE: 5
ggcggcagcg ccctgccgac gcc                                                 23

<210> SEQ ID NO 6
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 6
cattgttttc caattctccc ct                                                  22

<210> SEQ ID NO 7
<211> LENGTH: 24
<212> TYPE: DNA
<213> ORGANISM: Artificial Sequence
<220> FEATURE:
<223> OTHER INFORMATION: Artificial Sequence: Synthetic Primer

<400> SEQUENCE: 7
cggcggagcc ccgccgcccg ccgc                                                24

<210> SEQ ID NO 8
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 8
tgaaactcag caacaaatcc ag                                                  22

<210> SEQ ID NO 9
<211> LENGTH: 18
<212> TYPE: DNA
<213> ORGANISM: Artificial Sequence
<220> FEATURE:
<223> OTHER INFORMATION: Artificial Sequence: Synthetic Primer

<400> SEQUENCE: 9
ggagaacttc taccagca                                                       18

<210> SEQ ID NO 10
<211> LENGTH: 25
<212> TYPE: DNA
<213> ORGANISM: Artificial Sequence
<220> FEATURE:
<223> OTHER INFORMATION: Artificial Sequence: Synthetic Primer

<400> SEQUENCE: 10
gacattctcc tcggtgtccg aggac                                               25

<210> SEQ ID NO 11
<211> LENGTH: 25
<212> TYPE: DNA
<213> ORGANISM: Artificial Sequence
<220> FEATURE:
```

<223> OTHER INFORMATION: Artificial Sequence: Synthetic Primer

<400> SEQUENCE: 11
cggactggga gcgagcgcgg cgcag                                       25

<210> SEQ ID NO 12
<211> LENGTH: 24
<212> TYPE: DNA
<213> ORGANISM: Artificial Sequence
<220> FEATURE:
<223> OTHER INFORMATION: Artificial Sequence: Synthetic Primer

<400> SEQUENCE: 12
gaaaaaaatt aggtaatgct aaaa                                        24

<210> SEQ ID NO 13
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 13
atggctacct ctcgatatga                                             20

<210> SEQ ID NO 14
<211> LENGTH: 19
<212> TYPE: DNA
<213> ORGANISM: Artificial Sequence
<220> FEATURE:
<223> OTHER INFORMATION: Artificial Sequence: Synthetic Primer

<400> SEQUENCE: 14
cactccggat taccttcat                                              19

<210> SEQ ID NO 15
<211> LENGTH: 33
<212> TYPE: DNA
<213> ORGANISM: Artificial Sequence
<220> FEATURE:
<223> OTHER INFORMATION: Artificial Sequence: Synthetic Primer

<400> SEQUENCE: 15
gatcgtcgac gcgccacccg gcttcagaat ggc                              33

<210> SEQ ID NO 16
<211> LENGTH: 33
<212> TYPE: DNA
<213> ORGANISM: Artificial Sequence
<220> FEATURE:
<223> OTHER INFORMATION: Artificial Sequence: Synthetic Primer

<400> SEQUENCE: 16
gatcgaattc ggtgaagctg ccagtgctat ccg                              33

<210> SEQ ID NO 17
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 17
catctccctc cggaaaggac ac                                          22

```
<210> SEQ ID NO 18
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 18
cggatgaaca cgccagtcgc                                           20

<210> SEQ ID NO 19
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 19
cctggccgga gccactagac                                           20

<210> SEQ ID NO 20
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 20
ctatactcag atccatcacc                                           20

<210> SEQ ID NO 21
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 21
ccagcagcct cccgcgacga tg                                        22

<210> SEQ ID NO 22
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 22
gaggggtcga tgcactctga gg                                        22

<210> SEQ ID NO 23
<211> LENGTH: 21
<212> TYPE: DNA
<213> ORGANISM: Artificial Sequence
<220> FEATURE:
<223> OTHER INFORMATION: Artificial Sequence: Synthetic Primer

<400> SEQUENCE: 23
gctaccaaca cagaaccaca c                                         21

<210> SEQ ID NO 24
<211> LENGTH: 22
<212> TYPE: DNA
<213> ORGANISM: Artificial Sequence
<220> FEATURE:
<223> OTHER INFORMATION: Artificial Sequence: Synthetic Primer
```

```
<400> SEQUENCE: 24
tgaaactcag caacaaatcc ag                                              22

<210> SEQ ID NO 25
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 25
ctcccggccc ccgccatttc                                                 20

<210> SEQ ID NO 26
<211> LENGTH: 22
<212> TYPE: DNA
<213> ORGANISM: Artificial Sequence
<220> FEATURE:
<223> OTHER INFORMATION: Artificial Sequence: Synthetic Primer

<400> SEQUENCE: 26
ctctgggaat actggcactt cg                                              22

<210> SEQ ID NO 27
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 27
ctgacccgac tcgctggcgc                                                 20

<210> SEQ ID NO 28
<211> LENGTH: 20
<212> TYPE: DNA
<213> ORGANISM: Artificial Sequence
<220> FEATURE:
<223> OTHER INFORMATION: Artificial Sequence: Synthetic Primer

<400> SEQUENCE: 28
ggagagggtg agattagggc                                                 20

<210> SEQ ID NO 29
<211> LENGTH: 72
<212> TYPE: DNA
<213> ORGANISM: Artificial Sequence
<220> FEATURE:
<223> OTHER INFORMATION: Artificial Sequence: Synthetic

<400> SEQUENCE: 29 cccccctcgag gtcgacgatg agcacagaaa gcatgatccg agatgtggaa ctggcagagg    60
aggcgctccc ca                                                         72
```